United States Patent
Chang et al.

(10) Patent No.: US 11,673,909 B2
(45) Date of Patent: Jun. 13, 2023

(54) FURANEONE GLYCOSIDE COMPOUND, PHARMACEUTICAL COMPOSITION THEREOF, PREPARATION METHOD THEREFOR, AND APPLICATION THEREOF

(71) Applicant: FUDAN UNIVERSITY, Shanghai (CN)

(72) Inventors: Jun Chang, Shanghai (CN); Lin Jin, Shanghai (CN); Heyanhao Zhang, Shanghai (CN); Tong Niu, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 17/786,133

(22) PCT Filed: Dec. 18, 2020

(86) PCT No.: PCT/CN2020/137471
§ 371 (c)(1),
(2) Date: Jun. 16, 2022

(87) PCT Pub. No.: WO2021/121362
PCT Pub. Date: Jun. 24, 2021

(65) Prior Publication Data
US 2023/0092001 A1    Mar. 23, 2023

(30) Foreign Application Priority Data
Dec. 20, 2019    (CN) .......................... 201911327063.7

(51) Int. Cl.
*C07H 17/04*    (2006.01)

(52) U.S. Cl.
CPC .......... *C07H 17/04* (2013.01); *C07B 2200/13* (2013.01)

(58) Field of Classification Search
None
See application file for complete search history.

(56) References Cited

FOREIGN PATENT DOCUMENTS

| CN | 104151379 A | 11/2014 |
| CN | 113004355 A | 6/2021 |

OTHER PUBLICATIONS

International Search Report (English and Chinese) issued in International Patent Application, No. PCT/CN2020/137471, dated Mar. 17, 2021; ISA/CN.
Written Opinion of the International Searching Authority (English and Chinese) issued in International Patent Application No. PCT/CN2020/137471, dated Mar. 17, 2021; ISA/CN.
Comte G. et al. "Two Furanone Glucoside Derivatives from Juniperus Phoenicea", Phytochemistry, Dec. 31, 1996, pp. 1329-1332, vol. 41. No. 5.
Comte G. et al. "Phoeniceroside. the First Natural Bis-Furanone Propane Derivative from *Juniperus phoenicea* L." Tetrahedron Letters, Dec. 31, 1996, pp. 2955-2958, vol. 37. No. 17.
Mayerl F. et al. "2,5-Dimethyl-4-Hydroxy-3(2H)-Furanone Glucoside: Isolation from Strawberries and Synthesis", Phytochemistry, Dec. 31, 1989, pp. 631-633, vol. 28. No. 2.
Nahrstedt A. et al. "Phenylpropanoid Glycosides, A Furanone Glucoside and Geniposidic Acid from Members of the Rubiaceae", Phytochemistry, Dec. 31, 1995, pp. 375-378, vol. 39. No. 2.
Stadler N.C. et al. "Absorption of 3(2H)-Furanones by Human Intestinal Epithelial Caco-2 Cells", Journal of Agricultural and Food Chemistry, Apr. 1, 2009, pp. 3949-3954, vol. 57. No. 9.

*Primary Examiner* — Layla D Berry
(74) *Attorney, Agent, or Firm* — Harness, Dickey & Pierce, P.L.C.

(57) ABSTRACT

Disclosed are a furaneone glycoside compound, a pharmaceutical composition thereof, a preparation method therefor, and an application thereof. Specifically disclosed are a compound as represented by formula A-1, a pharmaceutically acceptable salt thereof or a crystal form thereof. Also disclosed is a pharmaceutical composition, which comprises the compound as represented by formula A-1, the pharmaceutically acceptable salt thereof, and a pharmaceutical adjuvant. Also disclosed is an application of the compound as represented by formula A-1, the pharmaceutically acceptable salt thereof, the crystal form thereof, or the pharmaceutical composition in the preparation of drugs. The drugs are drugs for treating inflammatory bowel diseases. The furaneone glycoside compound has a good effect of treating inflammatory bowel diseases, particularly ulcerative colitis.

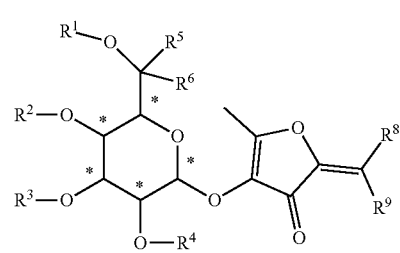

A-1

19 Claims, 2 Drawing Sheets

FURANEONE GLYCOSIDE COMPOUND, PHARMACEUTICAL COMPOSITION THEREOF, PREPARATION METHOD THEREFOR, AND APPLICATION THEREOF

CROSS-REFERENCE TO RELATED APPLICATIONS

This application is a U.S. National Phase Application under 35 U.S.C. 371 of International Application No. PCT/CN2020/137471, filed on Dec. 18, 2020, which claims the benefit of Chinese Patent Application No. 201911327063.7, filed on Dec. 20, 2019. The entire disclosures of the above applications are incorporated herein by reference.

TECHNICAL FIELD

The present invention relates to the field of pharmaceutical technology, and in particular, to a furaneone glycoside compound, a pharmaceutical composition thereof, a preparation method therefor, and use thereof.

BACKGROUND ART

Inflammatory bowel disease (IBD) is a chronic and recurrent intestinal inflammatory disease. Based on different pathological characteristics clinically, inflammatory bowel disease can be divided into two major categories, ulcerative colitis (UC) and Crohn's disease (CD). Ulcerative colitis is an inflammatory disease of the rectal and colonic mucosa, mainly affecting the mucosa and submucosa of the colon. Crohn's disease mainly affects the terminal ileum and adjacent colon and can involve the gastrointestinal tract in a phased and asymmetrical distribution. The incidence of inflammatory bowel diseases varies geographically. Northern Europe, the United Kingdom, and North America have the highest incidence of inflammatory bowel diseases, with a prevalence of 200-300/100,000. Asia and most developing countries have a lower prevalence of inflammatory bowel diseases, with a prevalence of 10-20/100,000. With the development of the economy, the incidence of inflammatory bowel diseases is on the rise in many newly industrialized countries in Africa, Asia, and South America. At the beginning of the 21st century, inflammatory bowel disease has become a global disease.

At present, there are many treatment options for inflammatory bowel diseases, but pharmacotherapy remains the mainstay for the treatment. Traditional aminosalicylic acids have been used to treat inflammatory bowel diseases for 50 years. However, aminosalicylic acids are not tolerated by more than 30% of patients, and aminosalicylic acids can cause side effects such as hepatic impairment, renal impairment, and gastrointestinal reaction. Thiopurines are currently the most widely used immunosuppressive agents for inflammatory bowel diseases. However, about 5% of patients using thiopurines have anaphylaxis, hepatic impairment, and myelosuppression, so it should be monitored throughout the treatment and reviewed regularly. Other biological agents, such as the human-mouse chimeric TNF-α monoclonal antibody infliximab, can improve the clinical symptoms and endoscopic lesions of Crohn's disease. However, infliximab is not widely used due to its high price and potential risks such as the increased likelihood of contracting tuberculosis. Therefore, it is urgent to develop new drugs with higher efficacy and fewer side effects for the treatment of inflammatory bowel diseases.

CONTENTS OF THE INVENTION

The technical problem to be solved by the present invention is to overcome the defect of the single structure of existing compounds for treating inflammatory bowel diseases, and provide a furaneone glycoside compound, a pharmaceutical composition thereof, a preparation method therefor, and use thereof. The furaneone glycoside compound has a good effect of treating inflammatory bowel diseases, particularly ulcerative colitis.

The present invention provides a compound represented by formula A-1, a pharmaceutically acceptable salt thereof, a solvate thereof, or a crystal form thereof,

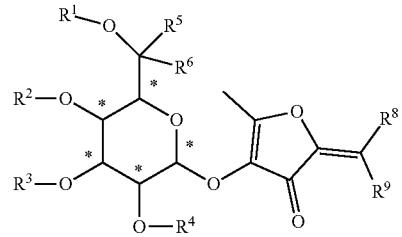

A-1 wherein $R^1$, $R^2$, $R^3$, and $R^4$ are independently hydrogen, $C_{1-4}$ alkyl, benzyl, —C(=O)R, or —C(=O)—O—R', and $R^1$, $R^2$, $R^3$, and $R^4$ are not simultaneously hydrogen;

each R' is independently $C_{1-4}$ alkyl;

each R is independently $C_{1-4}$ alkyl or phenyl;

$R^5$ and $R^6$ are independently hydrogen, or $R^5$ and $R^6$ are taken together to form =O;

$R^8$ and $R^9$ are independently $C_{1-4}$ alkyl;

alternatively, $R^8$ and $R^9$ are taken together with the carbon atom to which they are attached to form 3- to 7-membered cycloalkyl, 3- to 7-membered heterocycloalkyl, 3- to 7-membered cycloalkyl substituted with one or a plurality of $R^a$, or 3- to 7-membered heterocycloalkyl substituted with one or a plurality of $R^b$; in the 3- to 7-membered heterocycloalkyl and the 3- to 7-membered heterocycloalkyl substituted with one or a plurality of $R^b$, the heteroatoms in the 3- to 7-membered heterocycloalkyl are independently selected from N, O, and S, and the number of heteroatoms is independently 1, 2, or 3;

$R^a$ and $R^b$ are independently $C_{1-4}$ alkyl, —C(=O)R";

each R" is independently $C_{1-4}$ alkyl;

carbon atoms marked with "*" indicate that when the carbon atoms are chiral, the carbon atoms are in the R-configuration, S-configuration, or a mixture of R-configuration and S-configuration.

In the compound represented by formula A-1, the pharmaceutically acceptable salt thereof, the solvate thereof, or the crystal form thereof, certain groups are defined as follows (undefined groups are the same as above), when $R^1$, $R^2$, $R^3$, and $R^4$ are independently $C_{1-4}$ alkyl, then $C_{1-4}$ alkyl is methyl, ethyl, n-propyl, isopropyl, n-butyl, isobutyl, sec-butyl, or tert-butyl; preferably methyl.

In the compound represented by formula A-1, the pharmaceutically acceptable salt thereof, the solvate thereof, or the crystal form thereof, each R' is independently methyl, ethyl, n-propyl, isopropyl, n-butyl, isobutyl, sec-butyl, or tert-butyl; preferably ethyl.

In the compound represented by formula A-1, the pharmaceutically acceptable salt thereof, the solvate thereof, or the crystal form thereof, when each R is independently $C_{1-4}$ alkyl, then C$_{1-4}$ alkyl is methyl, ethyl, n-propyl, isopropyl, n-butyl, isobutyl, sec-butyl, or tert-butyl; preferably methyl or tert-butyl.

In the compound represented by formula A-1, the pharmaceutically acceptable salt thereof, the solvate thereof, or the crystal form thereof, when R$^8$ and R$^9$ are independently C$_{1-4}$ alkyl, then C$_{1-4}$ alkyl is methyl, ethyl, n-propyl, isopropyl, n-butyl, isobutyl, sec-butyl, or tert-butyl; preferably methyl.

In the compound represented by formula A-1, the pharmaceutically acceptable salt thereof, the solvate thereof, or the crystal form thereof, when R$^8$ and R$^9$ are taken together with the carbon atom to which they are attached to form 3- to 7-membered cycloalkyl or 3- to 7-membered cycloalkyl substituted with one or a plurality of R$^a$, then 3- to 7-membered cycloalkyl is a 5- to 6-membered cycloalkyl.

In the compound represented by formula A-1, the pharmaceutically acceptable salt thereof, the solvate thereof, or the crystal form thereof, when R$^8$ and R$^9$ are taken together with the carbon atom to which they are attached to form 3- to 7-membered heterocycloalkyl or 3- to 7-membered heterocycloalkyl substituted with one or a plurality of R$^b$, in the 3- to 7-membered heterocycloalkyl, then in the 3- to 7-membered heterocycloalkyl, the heteroatoms are independently selected from N and O, and the number of heteroatoms is independently 1.

In the compound represented by formula A-1, the pharmaceutically acceptable salt thereof, the solvate thereof, or the crystal form thereof, when R$^8$ and R$^9$ are taken together with the carbon atom to which they are attached to form 3- to 7-membered heterocycloalkyl or 3- to 7-membered heterocycloalkyl substituted with one or a plurality of R$^b$, wherein the 3- to 7-membered heterocycloalkyl is 5- to 6-membered heterocycloalkyl.

In the compound represented by formula A-1, the pharmaceutically acceptable salt thereof, the solvate thereof, or the crystal form thereof, when R$^8$ and R$^9$ are taken together with the carbon atom to which they are attached to form 3- to 7-membered heterocycloalkyl, then

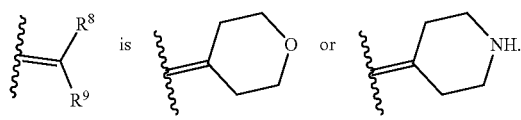

In the compound represented by formula A-1, the pharmaceutically acceptable salt thereof, the solvate thereof, or the crystal form thereof, when R$^a$ and R$^b$ are independently C$_{1-4}$ alkyl, then C$_{1-4}$ alkyl is methyl, ethyl, n-propyl, isopropyl, n-butyl, isobutyl, sec-butyl, or tert-butyl.

In the compound represented by formula A-1, the pharmaceutically acceptable salt thereof, the solvate thereof, or the crystal form thereof, each R" is independently methyl, ethyl, n-propyl, isopropyl, n-butyl, isobutyl, sec-butyl, or tert-butyl; preferably methyl.

In the compound represented by formula A-1, the pharmaceutically acceptable salt thereof, the solvate thereof, or the crystal form thereof, when R$^8$ and R$^9$ are taken together with the carbon atom to which they are attached to form 3- to 7-membered heterocycloalkyl substituted with one or a plurality of R$^b$, then

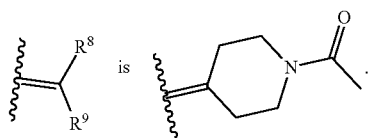

In the compound represented by formula A-1, the pharmaceutically acceptable salt thereof, the solvate thereof, or the crystal form thereof, R$^1$, R$^2$, R$^3$, and R$^4$ are independently hydrogen, C$_{1-4}$ alkyl, —C(=O)R, or —C(=O)—O—R'.

In the compound represented by formula A-1, the pharmaceutically acceptable salt thereof, the solvate thereof, or the crystal form thereof, R$^1$ is C$_{1-4}$ alkyl, —C(=O)R, or —C(=O)—O—R'; preferably C$_{1-4}$ alkyl or —C(=O)R.

In the compound represented by formula A-1, the pharmaceutically acceptable salt thereof, the solvate thereof, or the crystal form thereof, R$^1$ is methyl,

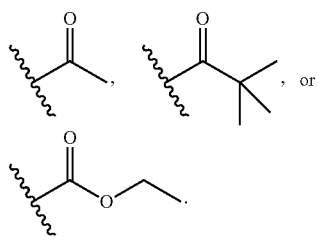

In the compound represented by formula A-1, the pharmaceutically acceptable salt thereof, the solvate thereof, or the crystal form thereof, R$^2$, R$^3$, and R$^4$ are independently hydrogen or —C(=O)R; preferably, R$^2$, R$^3$, and R$^4$ are independently —C(=O)R.

In the compound represented by formula A-1, the pharmaceutically acceptable salt thereof, the solvate thereof, or the crystal form thereof, R$^2$, R$^3$, and R$^4$ are independently hydrogen,

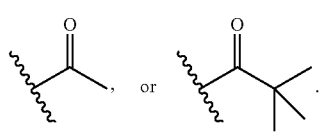

In the compound represented by formula A-1, the pharmaceutically acceptable salt thereof, the solvate thereof, or the crystal form thereof, R$^2$, R$^3$, and R$^4$ are the same group.

In the compound represented by formula A-1, the pharmaceutically acceptable salt thereof, the solvate thereof, or the crystal form thereof, when R$^5$ and R$^6$ are independently hydrogen, then R$^1$ is —C(=O)R

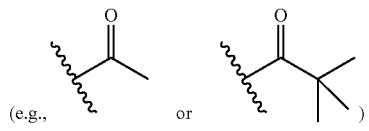

or —C(=O)—O—R'

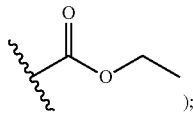 [SMILES: *C(=O)OCC]

when $R^5$ and $R^6$ are taken together to form =O, then $R^1$ is $C_{1-4}$ alkyl (e.g., methyl).

In the compound represented by formula A-1, the pharmaceutically acceptable salt thereof, the solvate thereof, or the crystal form thereof, each R is independently $C_{1-4}$ alkyl; preferably methyl or tert-butyl.

In the compound represented by formula A-1, the pharmaceutically acceptable salt thereof, the solvate thereof, or the crystal form thereof, $R^a$ and $R^b$ are independently —C(=O)R''; preferably

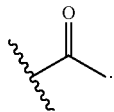

In the compound represented by formula A-1, the pharmaceutically acceptable salt thereof, the solvate thereof, or the crystal form thereof, $R^8$ and $R^9$ are independently $C_{1-4}$ alkyl, or $R^8$ and $R^9$ are taken together with the carbon atom to which they are attached to form 3- to 7-membered cycloalkyl, 3- to 7-membered heterocycloalkyl, or 3- to 7-membered heterocycloalkyl substituted with one or a plurality of $R^b$; preferably, $R^8$ and $R^9$ are independently $C_{1-4}$ alkyl, or $R^8$ and $R^9$ are taken together with the carbon atom to which they are attached to form 3- to 7-membered cycloalkyl or 3- to 7-membered heterocycloalkyl.

In the compound represented by formula A-1, the pharmaceutically acceptable salt thereof, the solvate thereof, or the crystal form thereof,

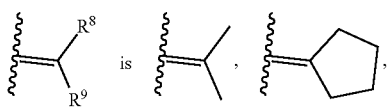

is

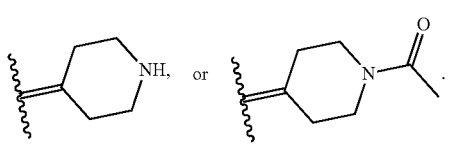

In a certain embodiment of the present invention,

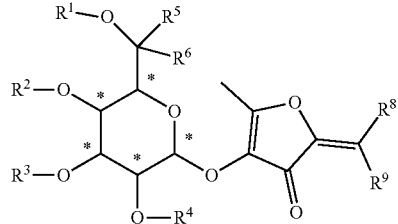

is

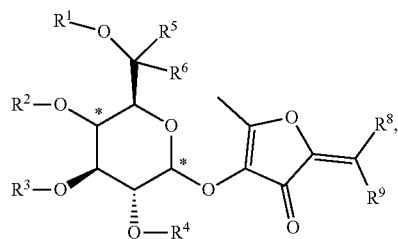

preferably

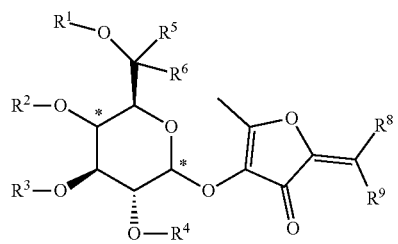

(i.e.,

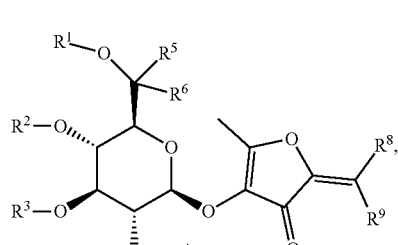

or a mixture of

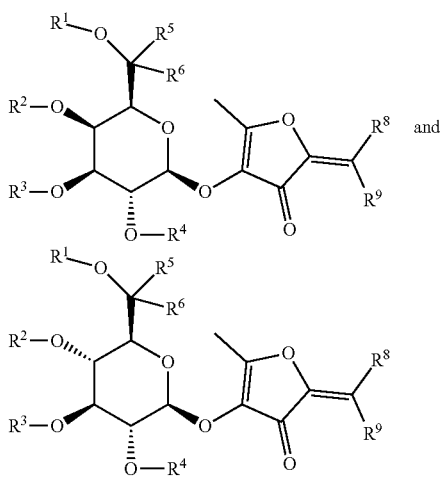

in a molar ratio of 1:1).

In the compound represented by formula A-1, the pharmaceutically acceptable salt thereof, the solvate thereof, or the crystal form thereof, the structure of the compound represented by formula A-1 is as follows:

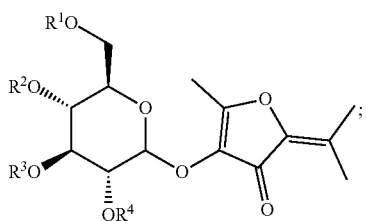

wherein $R^1$, $R^2$, $R^3$, and $R^4$ are independently hydrogen, $C_{1-4}$ alkyl, benzyl, or —C(=O)R, and $R^1$, $R^2$, $R^3$, and $R^4$ are not simultaneously hydrogen;

each R is independently $C_{1-4}$ alkyl or phenyl.

In the compound represented by formula A, certain groups are defined as follows (undefined groups are the same as above), preferably, $R^1$, $R^2$, $R^3$, and $R^4$ are independently hydrogen or —C(=O)R.

In the compound represented by formula A, certain groups are defined as follows (undefined groups are the same as above), preferably, each R is independently $C_{1-4}$ alkyl.

In the compound represented by formula A, preferably, $R^1$, $R^2$, $R^3$, and $R^4$ are hydrogen or —C(=O)R, each R is independently $C_{1-4}$ alkyl.

In the compound represented by formula A, when $R^1$, $R^2$, $R^3$, and $R^4$ are independently $C_{1-4}$ alkyl, then $C_{1-4}$ alkyl is preferably methyl, ethyl, n-propyl, isopropyl, n-butyl, isobutyl, sec-butyl, or tert-butyl.

In the compound represented by formula A, preferably, each R is independently methyl, ethyl, n-propyl, isopropyl, n-butyl, isobutyl, sec-butyl, tert-butyl, or phenyl, more preferably methyl.

In the compound represented by formula A, preferably, $R^1$, $R^2$, $R^3$, and $R^4$ are the same group.

The structure of the compound represented by formula A can be as follows:

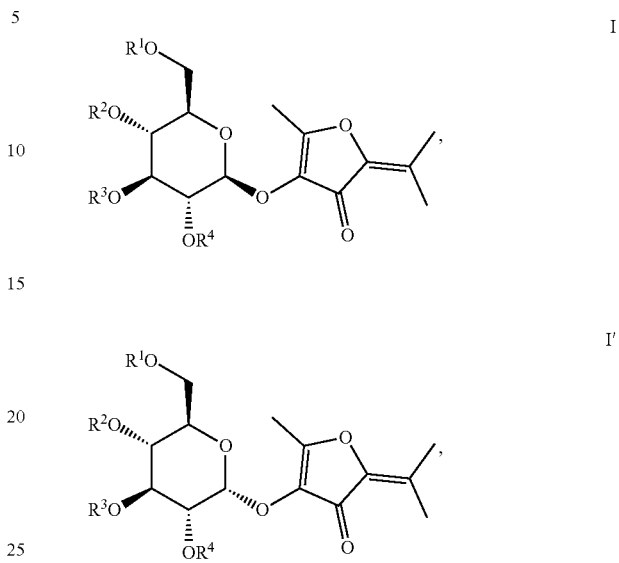

or a mixture of

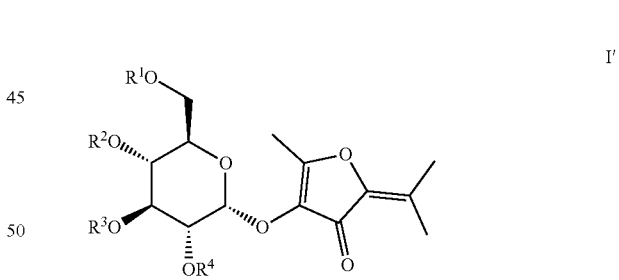

in a molar ratio of 1:1, the preferred structure is

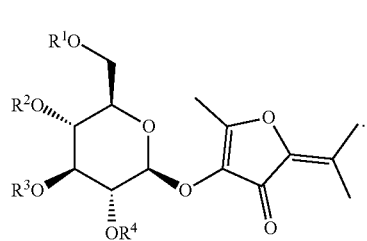

The compound represented by formula A-1 can be any of the following compounds,
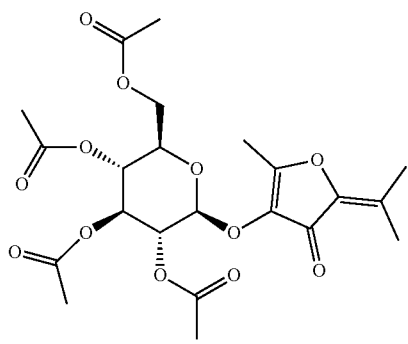
I-2
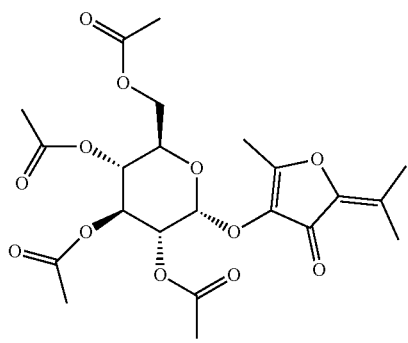
I'-2
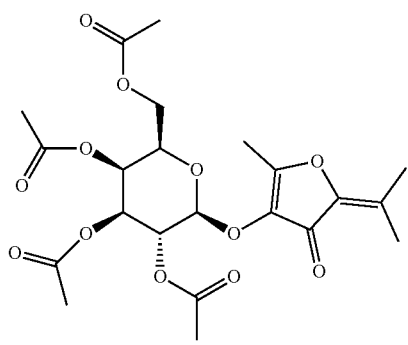
I-4
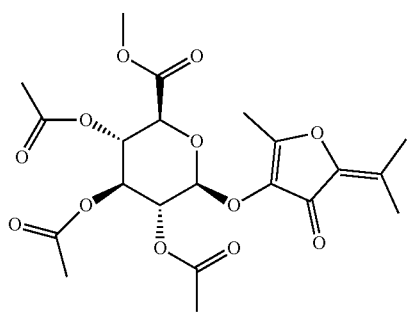
I-5
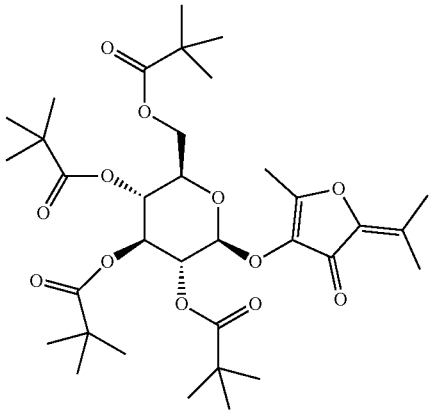
I-6
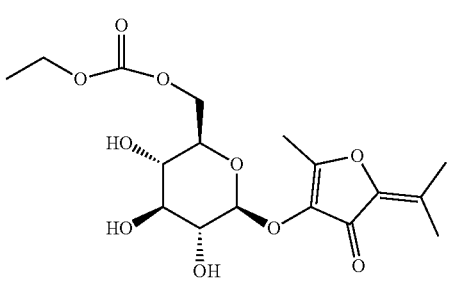
I-7
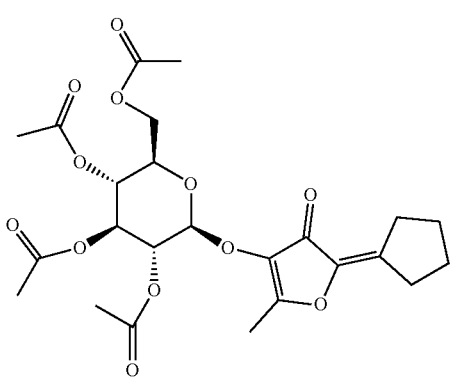
I-8
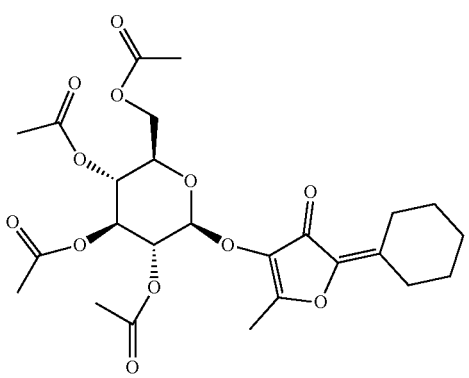
I-9

-continued

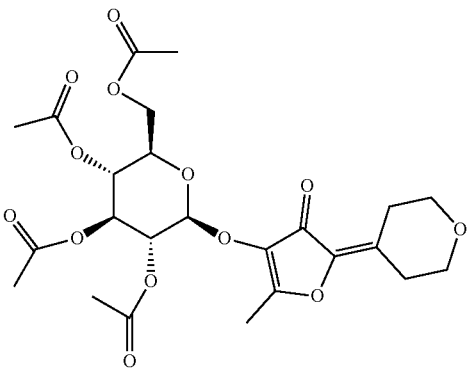

I-10

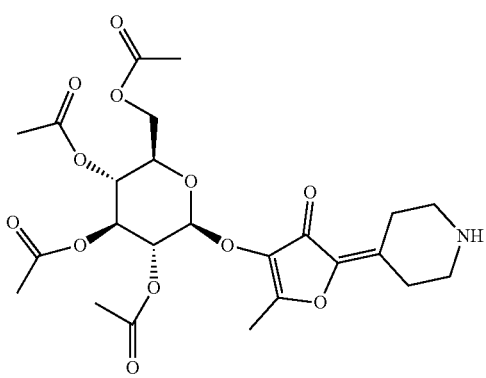

I-11

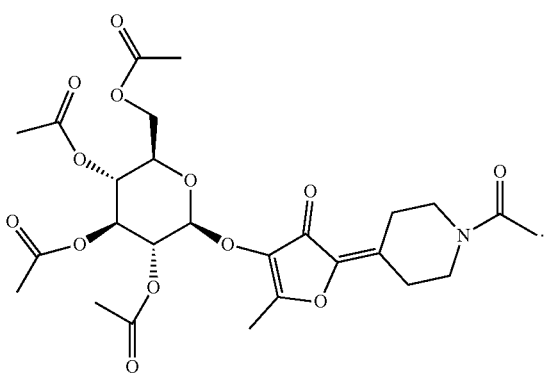

I-12

The present invention provides a pharmaceutical composition comprising the compound represented by formula A-1, the pharmaceutically acceptable salt thereof, the solvate thereof or the crystal form thereof, and a pharmaceutical adjuvant;

the structure of the compound represented by formula A-1 is as follows:

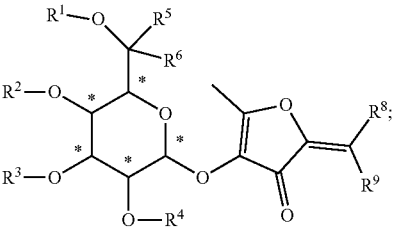

A-1 wherein $R^1$, $R^2$, $R^3$, and $R^4$ are independently hydrogen, $C_{1-4}$ alkyl, benzyl, —C(═O)R, or —C(═O)—O—R';

R, R', *, $R^5$, $R^6$, $R^8$, and $R^9$ are defined in any of previous embodiments above.

The pharmaceutical composition is preferably a pharmaceutical composition for treating inflammatory bowel diseases. The inflammatory bowel disease is preferably ulcerative colitis.

The present invention provides use of a compound represented by formula A-1, a pharmaceutically acceptable salt thereof, a solvate thereof, a crystal form thereof, or the above-mentioned pharmaceutical composition in the preparation of a medicament. The medicament is preferably a medicament for treating inflammatory bowel disease, more preferably for treating ulcerative colitis;

the structure of the compound represented by formula A-1 is as follows:

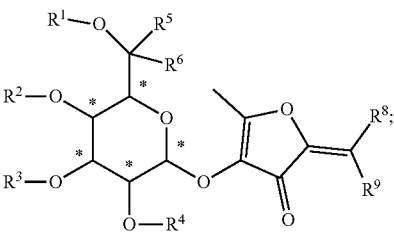

A-1 wherein $R^1$, $R^2$, $R^3$, and $R^4$ are independently hydrogen, $C_{1-4}$ alkyl, benzyl, —C(═O)R, or —C(═O)—O—R';

R, R', *, $R^5$, $R^6$, $R^8$, and $R^9$ are defined in any of the previous embodiments.

In the pharmaceutical composition or the use, certain groups are defined as follows (undefined groups are the same as above), when $R^1$, $R^2$, $R^3$, and $R^4$ are independently $C_{1-4}$ alkyl, then $C_{1-4}$ alkyl is methyl, ethyl, n-propyl, isopropyl, n-butyl, isobutyl, sec-butyl, or tert-butyl; preferably methyl.

In the pharmaceutical composition or the use, certain groups are defined as follows (undefined groups are the same as above), $R^1$, $R^2$, $R^3$, and $R^4$ are independently hydrogen, $C_{1-4}$ alkyl, —C(═O)R, or —C(═O)—O—R'.

In the pharmaceutical composition or the use, certain groups are defined as follows (undefined groups are the same as above), $R^1$ is $C_{1-4}$ alkyl, —C(═O)R, or —C(═O)—O—R'; preferably $C_{1-4}$ alkyl or —C(═O)R.

In the pharmaceutical composition or the use, certain groups are defined as follows (undefined groups are the same as above), $R^1$ is methyl,

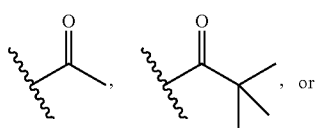, or

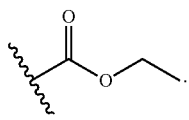.

In the pharmaceutical composition or the use, certain groups are defined as follows (undefined groups are the same as above), $R^2$, $R^3$, and $R^4$ are independently hydrogen or —C(=O)R; preferably, $R^2$, $R^3$, and $R^4$ are independently —C(=O)R.

In the pharmaceutical composition or the use, certain groups are defined as follows (undefined groups are the same as above), $R^2$, $R^3$, and $R^4$ are independently hydrogen,

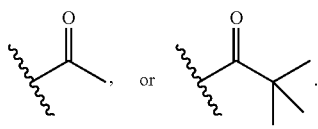.

In the pharmaceutical composition or the use, certain groups are defined as follows (undefined groups are the same as above), $R^2$, $R^3$, and $R^4$ are the same group.

In the pharmaceutical composition or the use, certain groups are defined as follows (undefined groups are the same as above), when $R^5$ and $R^6$ are independently hydrogen, then $R^1$ is —C(=O)R (e.g., 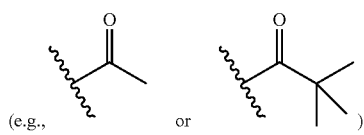)

or —C(=O)—O—R'

(e.g., 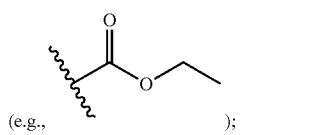 [SMILES: *C(=O)OCC]);

when $R^5$ and $R^6$ are taken together to form =O, then $R^1$ is $C_{1-4}$ alkyl (e.g., methyl).

In the pharmaceutical composition or the use, preferably,

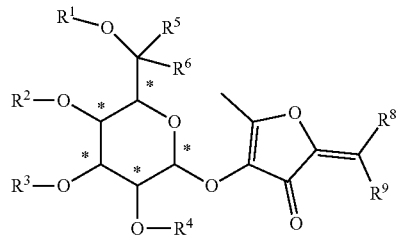    A-1 is

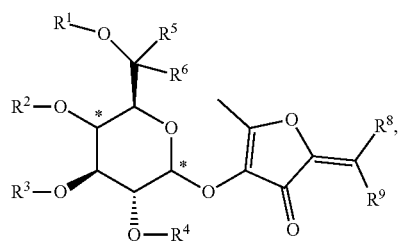, more preferably

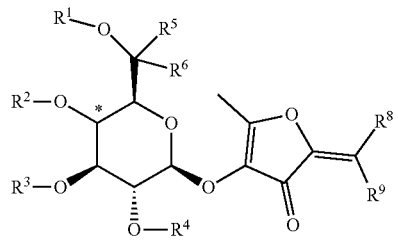

(i.e., 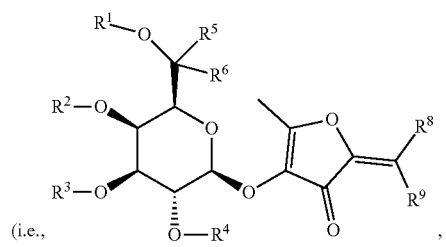,

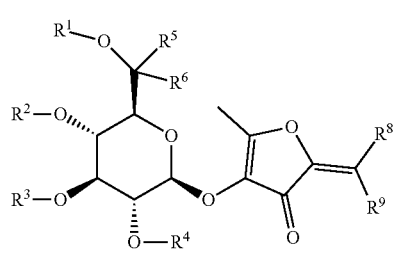

or a mixture of

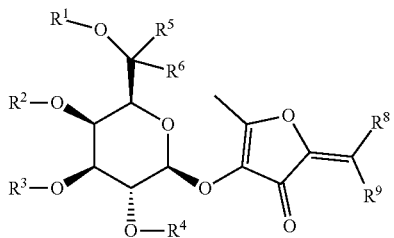

and

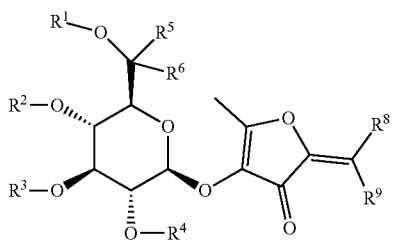

in a molar ratio of (1:1).

In the pharmaceutical composition or the use, certain groups are defined as follows (undefined groups are the same as above), the structure of the compound represented by formula A-1 is as follows:

A

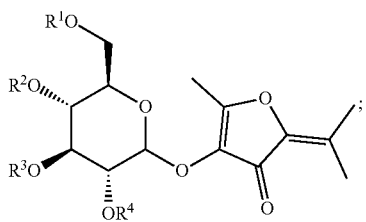

wherein $R^1$, $R^2$, $R^3$, and $R^4$ are independently hydrogen, $C_{1-4}$ alkyl, benzyl, or —C(=O)R;

R is defined in any of previous embodiments above.

In the pharmaceutical composition or the use, certain groups are defined as follows (undefined groups are the same as above), preferably, $R^1$, $R^2$, $R^3$, and $R^4$ are independently hydrogen or —C(=O)R.

In the pharmaceutical composition or the use, preferably, $R^1$, $R^2$, $R^3$, and $R^4$ are independently hydrogen or —C(=O)R, each R is independently $C_{1-4}$ alkyl.

In the pharmaceutical composition or the use, when $R^1$, $R^2$, $R^3$, and $R^4$ are independently $C_{1-4}$ alkyl, then $C_{1-4}$ alkyl is preferably methyl, ethyl, n-propyl, isopropyl, n-butyl, isobutyl, sec-butyl or tert-butyl.

In the pharmaceutical composition or the use, preferably, $R^1$, $R^2$, $R^3$, and $R^4$ are the same group.

In the pharmaceutical composition or the use, the structure of the compound represented by formula A can be as follows:

I

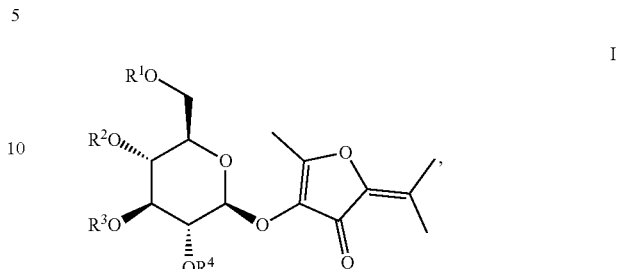

I'

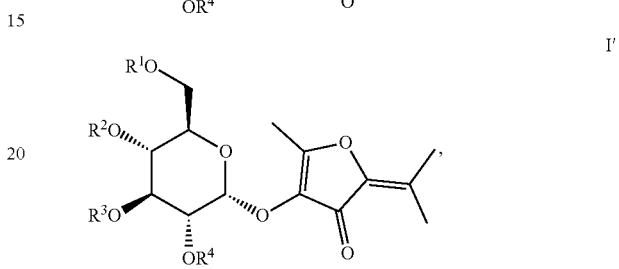

or a mixture of

I

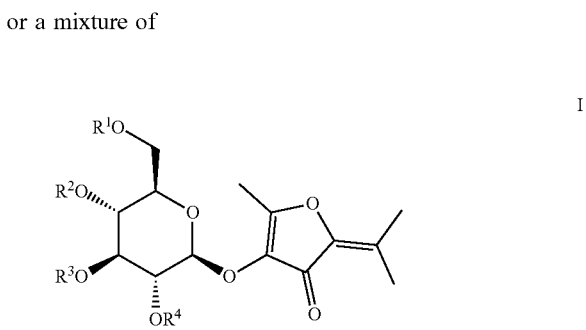

and

I'

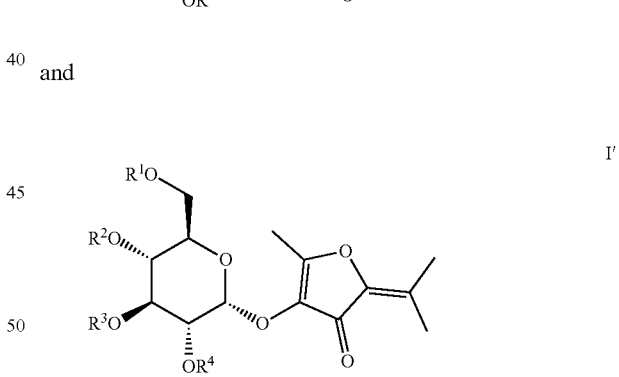

in a molar ratio of 1:1, the preferred structure is

I

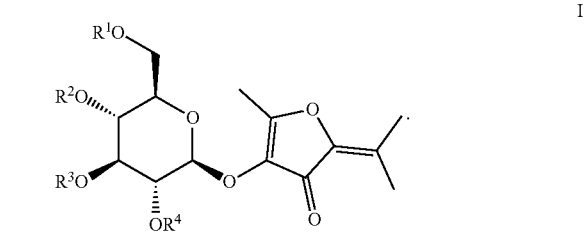

In the pharmaceutical composition or the use, the compound represented by formula A-1 can be any of the following compounds:
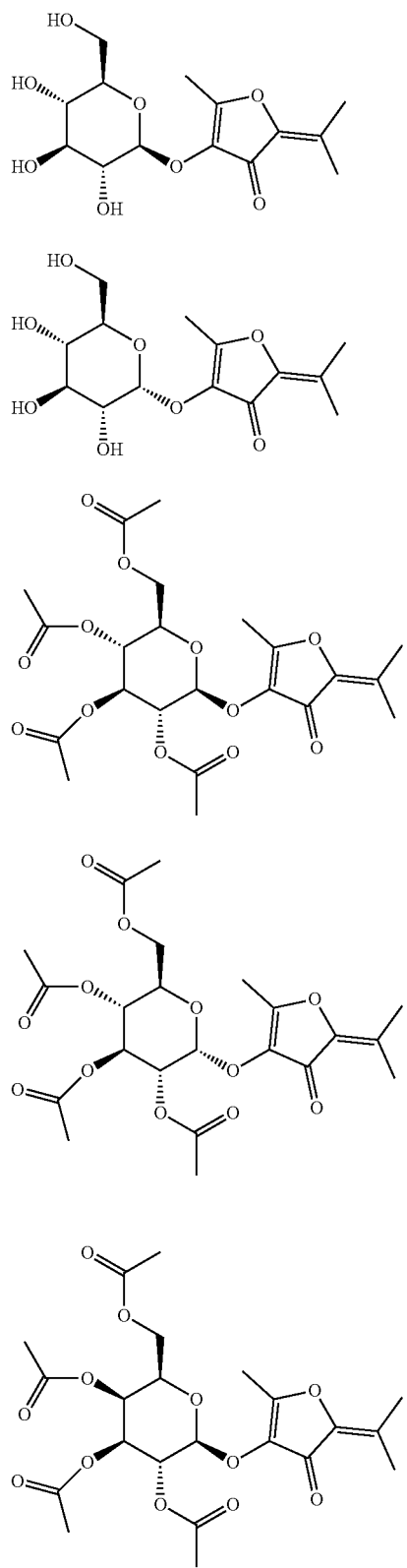
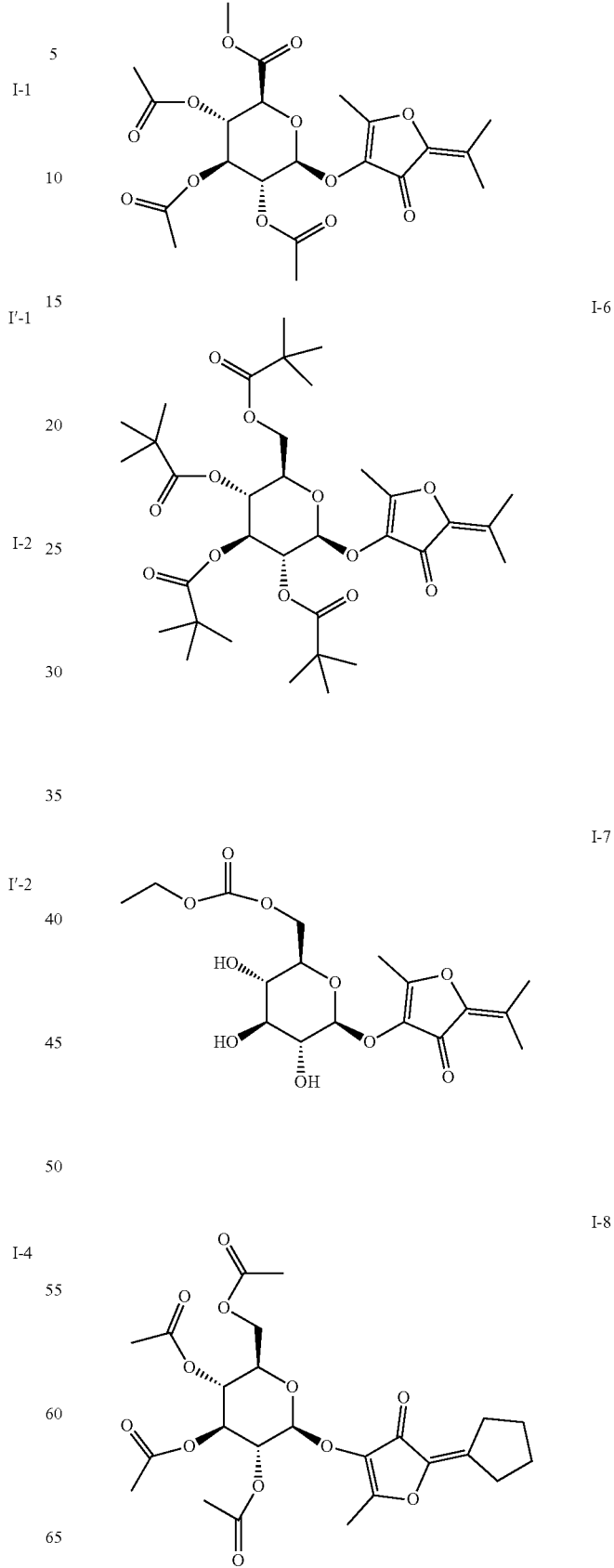

-continued

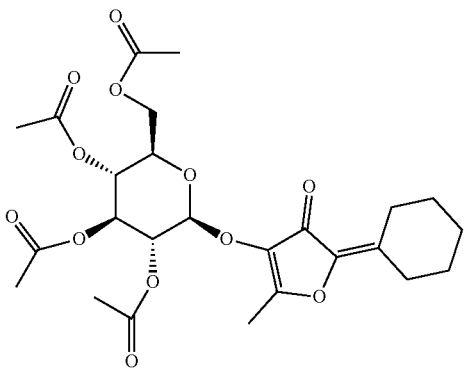

I-9

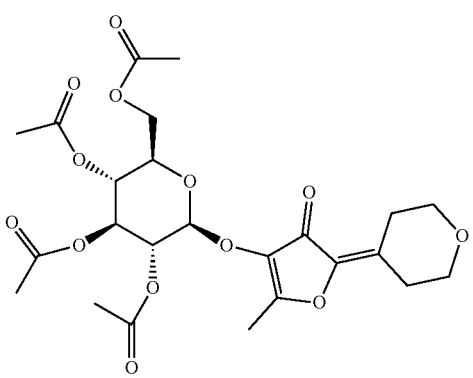

I-10

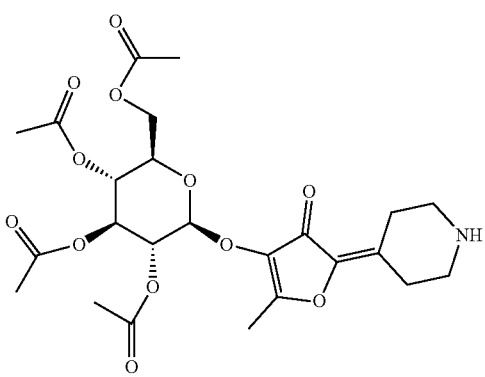

I-11

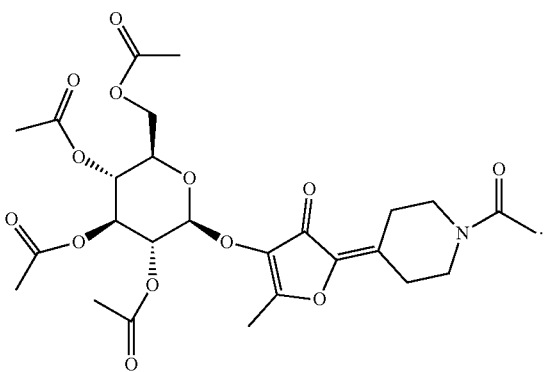

I-12

The present invention provides a crystal form of the compound represented by formula I-2,

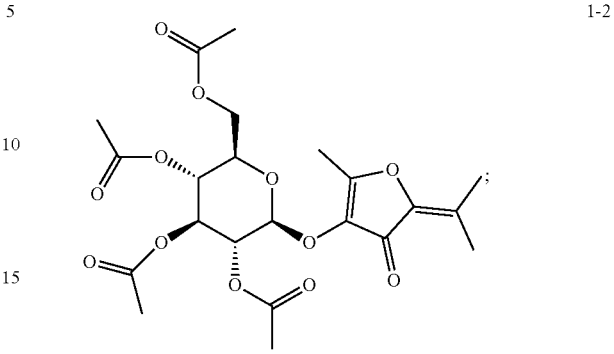

I-2 the unit cell parameters of the compound represented by formula I-2 are: a=10.5391(3) Å, α=90°; b=14.2167(4) Å, β=90°; c=15.9116(5) Å, γ=90°; space group $P2_12_12_1$; preferably:

| | |
|---|---|
| Empirical formula | $C_{22}H_{28}O_{12}$ |
| Formula weight | 484.44 |
| Temperature | 169.99K |
| Wavelength | 1.34139 Å |
| Crystal system | Orthorhombic system |
| Space group | $P2_12_12_1$ |
| Unit cell dimensions | a = 10.5391(3) Å, α = 90° |
| | b = 14.2167(4) Å, β = 90° |
| | c = 15.9116(5) Å, γ = 90° |
| Unit cell volume | 2384.05(12) Å$^3$ |
| Z | 4 |
| Density (calculated) | 1.350 Mg/m$^3$ |
| Absorption coefficient | 0.607 mm$^{-1}$ |
| F(000) | 1024 |
| Crystal size | 0.12 × 0.1 × 0.05 mm$^3$ |
| Theta range for data collection | 5.148 to 54.935° |
| Index ranges | −12 <= h <= 12, −15 <= k <= 17, |
| | −19 <= l <= 19 |
| Reflections collected | 21844 |
| Independent reflections | 4478 [R(int) = 0.0451] |
| Refinement method | Full-matrix least-squares on F$^2$ |

The present invention provides a pharmaceutical composition comprising a crystal form of the compound represented by formula I-2 and a pharmaceutical adjuvant. The pharmaceutical composition is preferably a pharmaceutical composition for treating inflammatory bowel disease, wherein the inflammatory bowel disease is preferably ulcerative colitis.

The present invention provides use of the crystal form of the compound represented by formula I-2 or the pharmaceutical composition in the preparation of a medicament. The medicament is preferably a medicament for treating inflammatory bowel disease, more preferably for treating ulcerative colitis.

The present invention provides a method of preparing the compound represented by formula A-1, comprising the steps of any of the following methods:

method A:

in a solvent, in the presence of a catalyst, a compound represented by formula B-1 and a compound represented by formula C-1 are subjected to an ether-forming reaction shown below to obtain the compound represented by formula A-1;

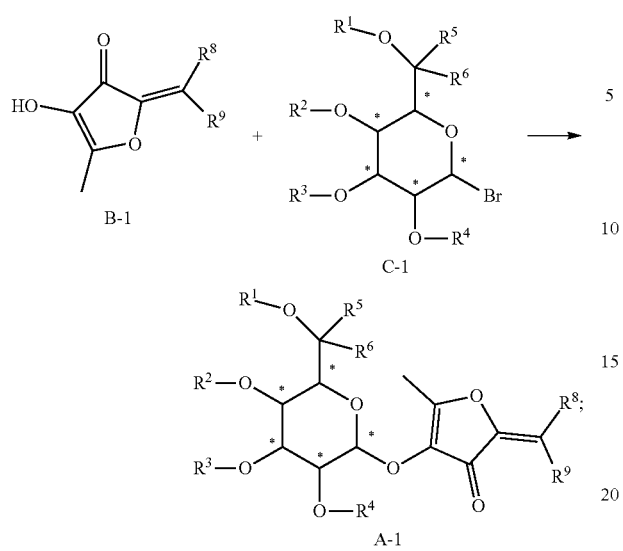

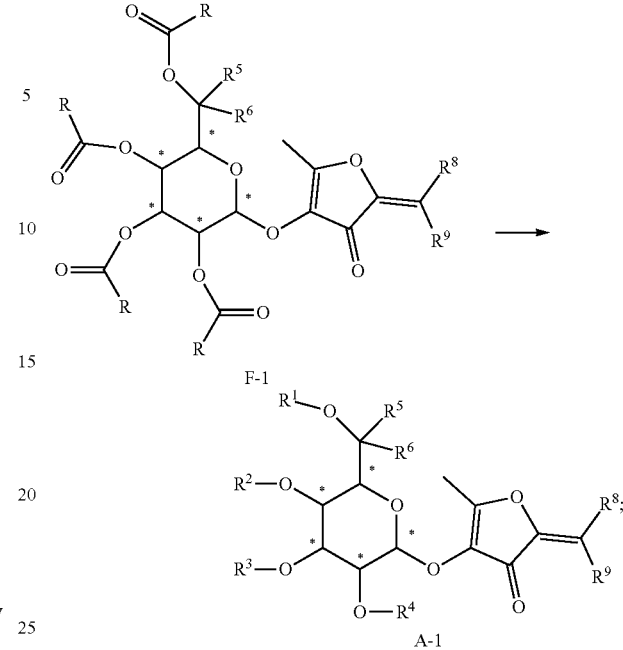

in the method A, $R^1$, $R^2$, $R^3$, and $R^4$ are independently $C_{1-4}$ alkyl, benzyl, —C(=O)R, or —C(=O)—O—R';

R, R', *, $R^5$, $R^6$, $R^8$, and $R^9$ are defined in any of the previous embodiments; method B:

in a solvent, a compound represented by formula D-1 and a compound represented by formula E-1 are subjected to a reaction shown below to obtain the compound represented by formula A-1;

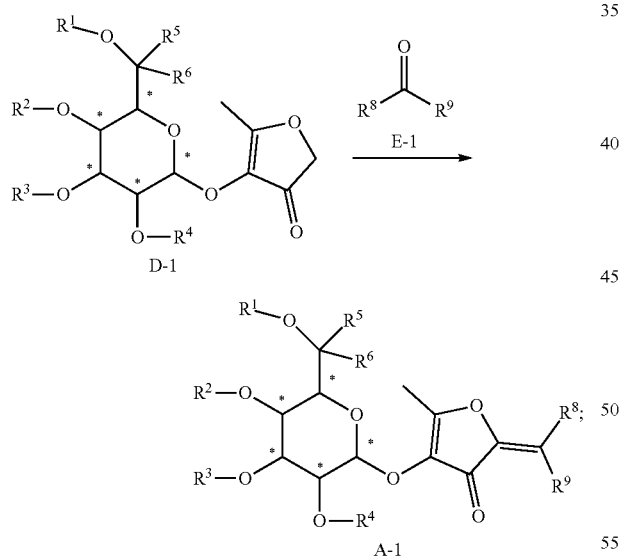

in the method B, $R^1$, $R^2$, $R^3$, and $R^4$ are independently $C_{1-4}$ alkyl, benzyl, —C(=O)R, or —C(=O)—O—R'; $R^8$ and $R^9$ are independently $C_{1-4}$ alkyl;

R, R', *, $R^5$, and $R^6$ are defined in any of the previous embodiments; method C:

in a solvent, in the presence of a base, a compound represented by formula F-1 is subjected to a hydrolysis reaction shown below to obtain the compound represented by formula A-1;

in the method C, $R^1$, $R^2$, $R^3$, and $R^4$ are hydrogen;

R, *, $R^5$, $R^6$, $R^8$, and $R^9$ are defined in any of the previous embodiments;

method D:

in a solvent, in the presence of a catalyst, a compound represented by formula G-1 and a compound represented by formula G-2 are subjected to a substitution reaction shown below to obtain the compound represented by formula A-1;

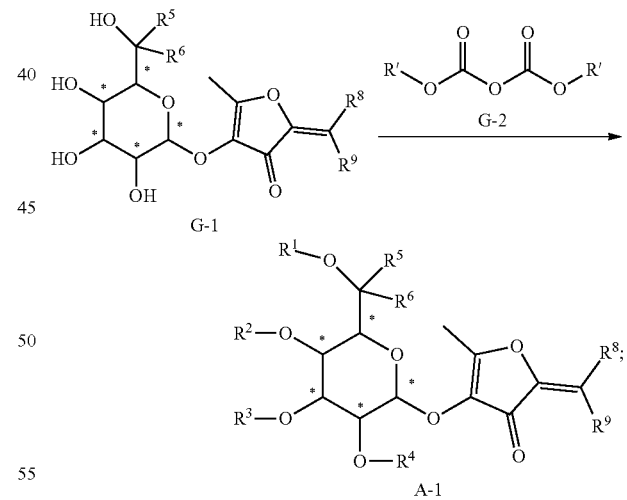

in the method D, $R^2$, $R^3$, and $R^4$ are hydrogen;

R', *, $R^5$, $R^6$, $R^8$, and $R^9$ are defined in any of the previous embodiments.

In a certain embodiment, in the method A, the conditions and operations of the ether-forming reaction can be conventional conditions and operations of this type of reaction in the art.

In a certain embodiment, in the method B, the conditions and operations of the reaction can be conventional conditions and operations of this type of reaction in the art.

In a certain embodiment, in the method C, the conditions and operations of the hydrolysis reaction can be conventional conditions and operations of this type of reaction in the art.

In a certain embodiment, in the method D, the conditions and operations of the substitution reaction can be conventional conditions and operations of this type of reaction in the art.

In a certain embodiment, the described method A includes the following steps: in the solvent, in the presence of the catalyst, a compound represented by formula B and a compound represented by formula C are subjected to the ether-forming reaction shown below to obtain a compound represented by formula I-3;

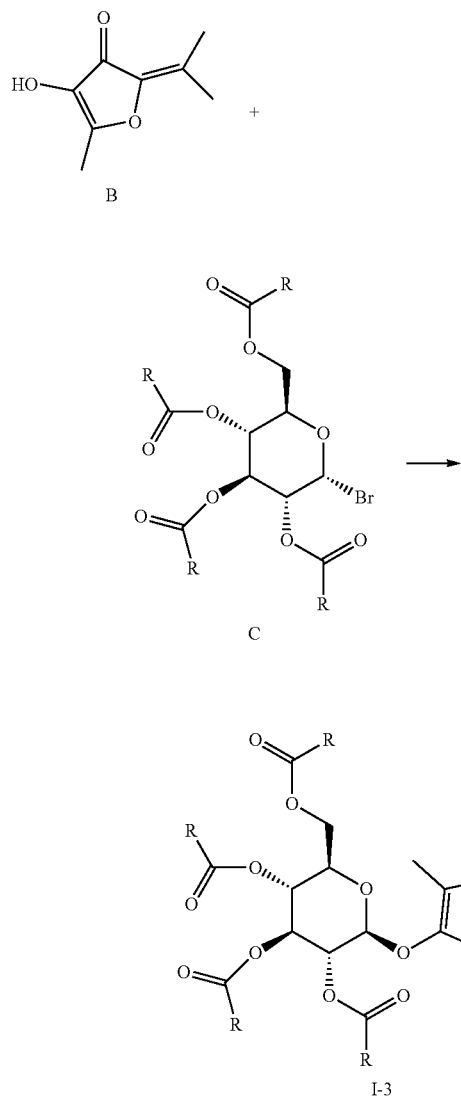

wherein R is defined in any of the embodiments.

In a certain embodiment, the described method B includes the following steps: in the solvent, a compound represented by formula D and acetone are subjected to the reaction shown below to obtain the compound represented by formula I-3;

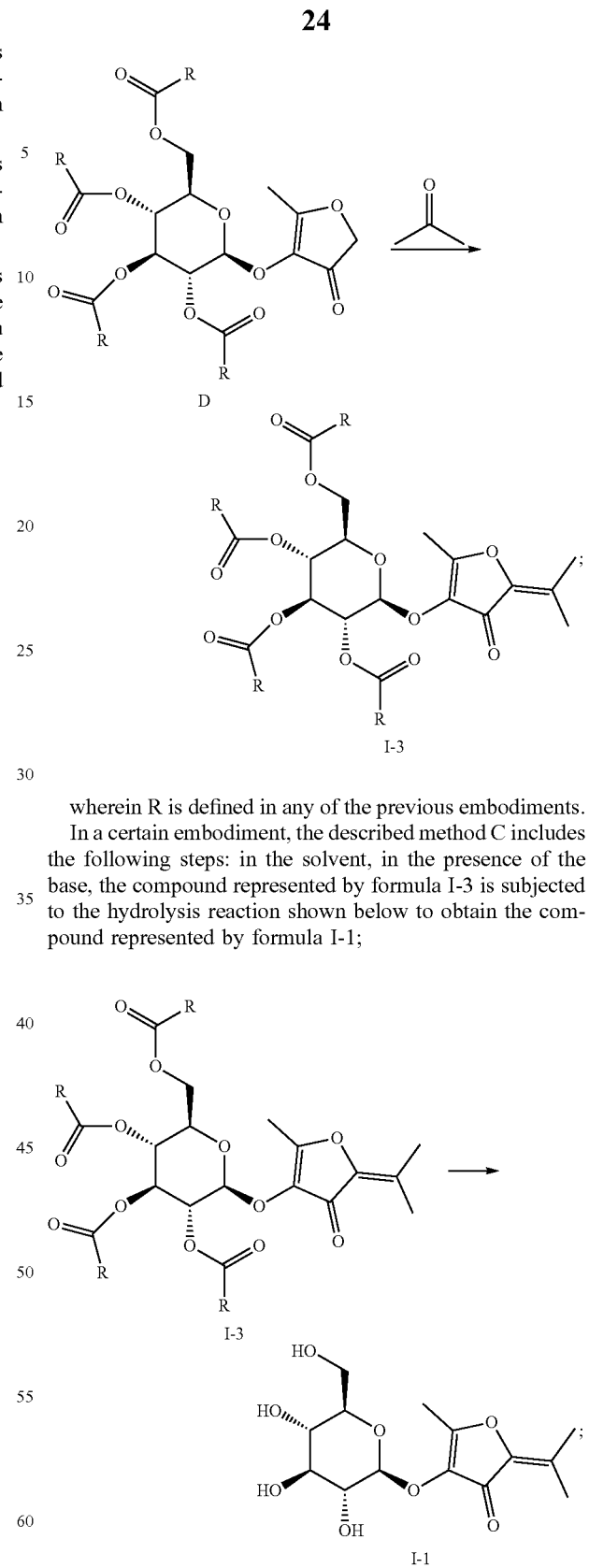

wherein R is defined in any of the previous embodiments.

In a certain embodiment, the described method C includes the following steps: in the solvent, in the presence of the base, the compound represented by formula I-3 is subjected to the hydrolysis reaction shown below to obtain the compound represented by formula I-1;

wherein R is defined in any of the previous embodiments.

The present invention provides a method of treating inflammatory bowel disease comprising administrating a therapeutically effective amount of substance A to a patient;

the substance A comprises the compound represented by formula A-1, the pharmaceutically acceptable salt thereof, the solvate thereof, the crystal form thereof, or the pharmaceutical composition thereof;

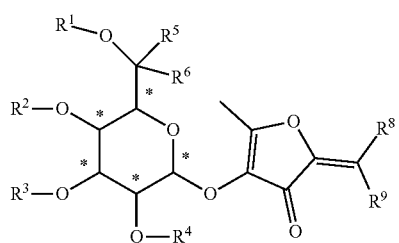

wherein the compound represented by formula A-1 is the same as any embodiment of the compound represented by formula A-1 in the pharmaceutical composition.

In the method of treating inflammatory bowel disease, the inflammatory bowel disease is preferably ulcerative colitis.

Unless otherwise specified, the terms used in the present invention shall have the following meanings:

Those skilled in the art can understand that, according to the conventions used in the art, the " ⟋⟍ " used in the structural formula of the group means that the corresponding group is connected to other fragments or groups in the compound through this site.

As used herein, the term "plurality" refers to 2, 3, 4, or 5, preferably 2 or 3.

When any variable (e.g., $R^b$) appears multiple times in the definition of a compound, the definition that appears at each position of the variable is independent of the definitions that appear at other positions, and their meanings are independent of each other and do not affect each other. Thus, if a group is substituted with 1, 2, or 3 $R^b$ groups, the group may be substituted with up to 3 $R^b$ groups, the definition of $R^b$ at that position is independent of the definition of $R^b$ at the remaining positions. Additionally, the combination of substituents and/or variables is permissible only if the combination produces a stable compound.

The pharmaceutical adjuvants described in the present invention can be those widely used in the field of pharmaceutical production. Adjuvants are primarily used to provide a safe, stable, and functional pharmaceutical composition, and may also provide methods to enable the active ingredient to dissolve at a desired rate after the subject has received administration or to facilitate effective absorption of the active ingredient after the subject has received administration of the composition. The pharmaceutical adjuvants can be inert fillers or provide some function, such as stabilizing the overall pH of the composition or preventing degradation of the active ingredients of the composition. The pharmaceutical adjuvants may include one or more of the following adjuvants: binder, suspending agent, emulsifying agent, diluting agent, stuffing bulking agent, granulating agent, adhesive agent, disintegrating agent, lubricant, anti-adhesive agent, flow aid, wetting agent, gelling agent, absorption retardant, dissolution inhibitor, enhancer, adsorbent, buffering agent, chelating agent, preservative, coloring agent, flavoring agent, and sweetening agent.

The pharmaceutical compositions of the present invention can be prepared according to the disclosure using any method known to those skilled in the art. For example, conventional mixing, dissolving, granulating, emulsifying, levigating, encapsulating, embedding, or lyophilizing processes.

The pharmaceutical compositions of the present invention can be administered in any form, including injection (intravenous), mucosal, oral (solid and liquid preparations), inhalation, ophthalmic, rectal, topical, or parenteral (infusion, injection, implant, subcutaneous, intravenous, intraarterial, intramuscular) administration. The pharmaceutical compositions of the present invention may also be in controlled-release or delayed-release forms (e.g., liposomes or microspheres). Examples of solid oral preparations include, but are not limited to, powders, capsules, caplets, softgels, and tablets, such as enteric-coated tablets or capsules. Examples of liquid preparations for oral or mucosal administration include, but are not limited to, suspensions, emulsions, elixirs, and solutions. Examples of topical preparations include, but are not limited to, emulsions, gels, ointments, creams, patches, pastes, foams, lotions, drops, or serum preparations. Examples of preparations for parenteral administration include, but are not limited to, solutions for injection, dry preparations that can be dissolved or suspended in a pharmaceutically acceptable vehicle, suspensions for injection and emulsions for injection. Examples of other suitable preparations of the pharmaceutical composition include, but are not limited to, eye drops and other ophthalmic preparations; aerosols: such as nasal sprays or inhalants; liquid preparations for parenteral administration; suppositories and lozenges.

As used herein, the term "pharmaceutically acceptable salt" refers to a salt of a compound of the present invention prepared with a relatively non-toxic, pharmaceutically acceptable acid or base. When the compounds of the present invention contain relatively acidic functional groups, base addition salts can be formed by contacting the neutral forms of such compounds with a sufficient amount of a pharmaceutically acceptable base in a neat solution or a suitable inert solvent. The pharmacologically acceptable base addition salts include, but are not limited to lithium, sodium, potassium, calcium, aluminum, magnesium, zinc, bismuth, ammonium, diethanolamine salts. When the compounds of the present invention contain relatively basic functional groups, acid addition salts can be formed by contacting the neutral forms of such compounds with a sufficient amount of a pharmaceutically acceptable acid in a neat solution or a suitable inert solvent. The pharmaceutically acceptable acids include inorganic acids, including but not limited to: hydrochloric acid, hydrobromic acid, hydroiodic acid, nitric acid, carbonic acid, phosphoric acid, phosphorous acid, sulfuric acid, etc. The pharmaceutically acceptable acids include organic acids, including but not limited to: acetic acid, propionic acid, oxalic acid, isobutyric acid, maleic acid, malonic acid, benzoic acid, succinic acid, octanedioic acid, (E)-butenedioic acid, lactic acid, mandelic acid, phthalic acid, benzenesulfonic acid, p-toluenesulfonic acid, citric acid, salicylic acid, tartaric acid, methanesulfonic acid, isonicotinic acid, acid citric acid, oleic acid, tannic acid, pantothenic acid, tartaric acid hydrogen, ascorbic acid, gentianic acid, fumaric acid, gluconic acid, glycolic acid, formic acid, pamoic acid (i.e., 4,4'-methylene-bis(3-hydroxy-2-naphthoic acid)), amino acids (e.g., glutamic acid, arginine), etc. When the compounds of the present invention contain relatively acidic and relatively basic functional groups, they can be converted into base addition salts or acid addition salts. For details, refer to Berge et al., "Pharmaceutical Salts", Journal of Pharmaceutical Science 66: 1-19 (1977), or, Handbook of Pharmaceutical Salts: Properties, Selection, and Use (P. Heinrich Stahl and Camille G. Wermuth, ed., Wiley-VCH, 2002).

As used herein, the term "solvate" refers to a substance formed by combining a compound of the present invention with a stoichiometric or non-stoichiometric amount of a solvent. Solvent molecules in solvates can exist in ordered or non-ordered arrangements. The solvent includes but is not limited to, water, methanol, ethanol, etc.

As used herein, the term "crystal form" refers to that the ions or molecules are arranged in a definite, repeating pattern in three-dimension space and have the regularity of periodic arrangement at a certain distance. Due to the differences in the periodic arrangement of ions or molecules, more than one crystal form can exist, i.e., polymorphism.

As used herein, the term "treatment" refers to therapeutic therapy. Concerning a specific condition, treatment refers to: (1) alleviating one or more biological manifestations of a disease or condition, (2) interfering with (a) one or more points in the biological cascade leading to or causing the condition, or (b) one or more biological manifestations of the condition, (3) ameliorating one or more symptoms, effects, or side effects associated with the condition, or one or more symptoms, effects, or side effects associated with the condition or the treatment, or (4) slowing the development of the condition or one or more biological manifestations of the condition.

As used herein, the term "therapeutically effective amount" refers to an amount of a compound that, when administered to a patient, is sufficient to effectively treat the disease or condition described herein. A "therapeutically effective amount" will vary depending on the compound, the condition, the severity of the condition, and the age of the patient to be treated, but can be adjusted as needed by those skilled in the art.

As used herein, the term "patient" refers to any animal, preferably a mammal, and most preferably a human, which is about to receive or has received the compound or composition according to an example of the present invention. The term "mammal" includes any mammal. Examples of mammals include, but are not limited to, cows, horses, sheep, pigs, cats, dogs, mice, rats, rabbits, guinea pigs, monkeys, humans, etc., with humans being the most preferred.

Based on not violating common knowledge in the art, the preferred conditions above can be combined arbitrarily to obtain examples of the present invention.

The reagents and raw materials used in the present invention are all commercially available.

The positive effect of the invention is that the furaneone glycoside compound has a good therapeutic effect on inflammatory bowel disease, particularly ulcerative colitis.

MODE OF CARRYING OUT THE INVENTION

Figure 1:
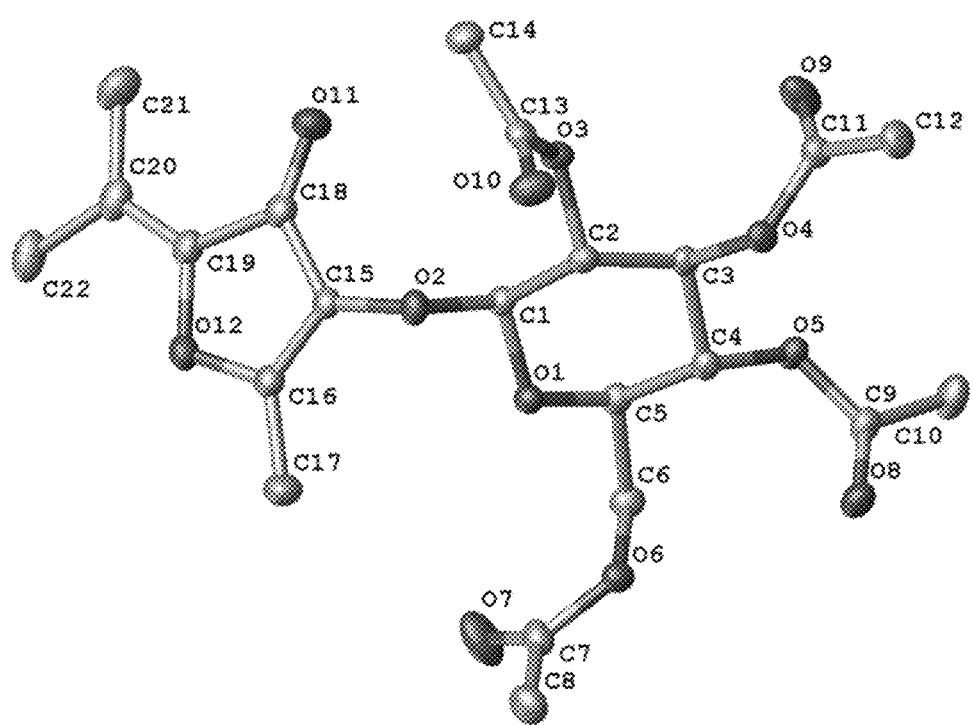
FIG. 1 is the crystal structure of compound I-2.

The present invention is further described below by way of examples, but the present invention is not limited to the scope of the described examples. The experimental methods that do not specify specific conditions in the following examples are selected according to conventional methods and conditions, or according to the product operation instruction.

Example 1

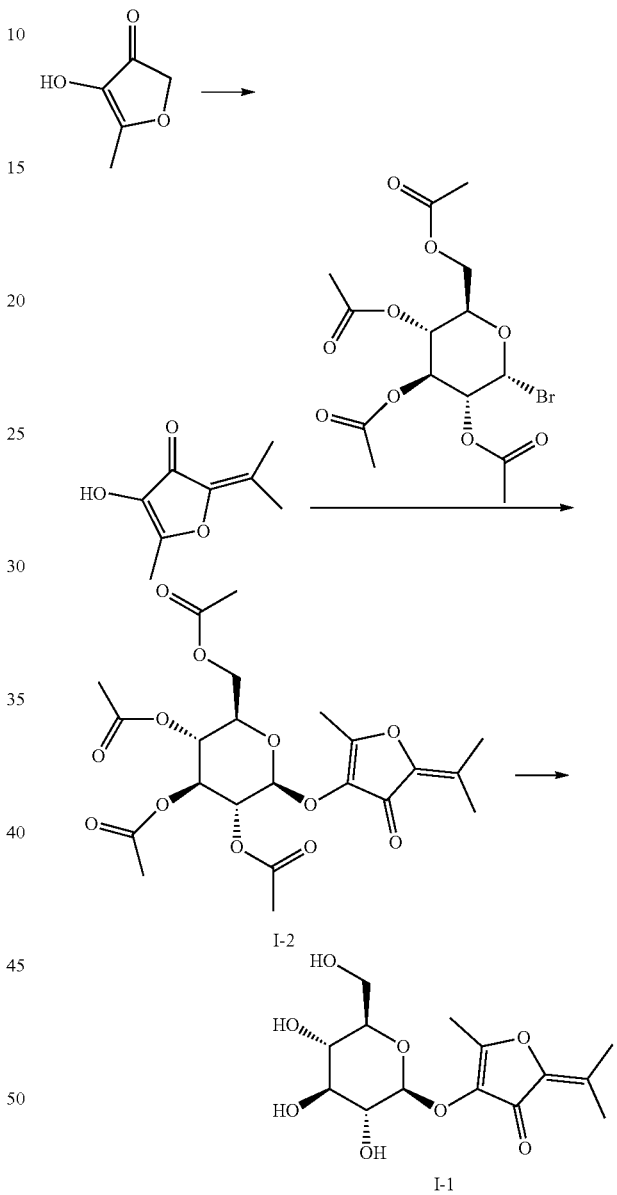

Step 1: 4-Hydroxy-5-methyl-3(2H)-furanone (1.14 g, 10 mmol, CAS: 19322-27-1), copper acetate (905 mg, 5 mmol), and sodium acetate (680 mg, 5 mmol) were dissolved in 10 mL of acetone and 30 mL of glacial acetic acid, heated to 50° C., stirred and refluxed for 1 hour; then diluted with 150 mL of water, and extracted the product with 100 mL of petroleum ether. the crude product was concentrated and chromatographed on silica gel (ethyl acetate/petroleum ether: 1/2) to give 4-hydroxy-5-methyl-2-(1-methylethylidene)-3 (2H)-furanone (1.23 g, 80% yield). $^1$H NMR (400 MHz, CD$_3$OD) δ (ppm): 2.36 (s, 3H), 2.31 (s, 3H), 2.05 (s, 3H). ESI-MS: 155 [M+1]$^+$.

Step 2: 4-Hydroxy-5-methyl-2-(1-methylethylidene)-3 (2H)-furanone (1.54 g, 10 mmol), 2,3,4,6-tetra-O-acetyl-α-D-glucopyranosyl bromide (6.15 g, 15 mmol, CAS: 572 8), and tetrabutylammonium bromide (4.83 g, 15 mmol, CAS: 1643-19-2) were dissolved in 50 mL of dichloromethane and heated to 35° C.; 75 mL of NaOH aqueous solution (1 mol/L) was further added. After stirring for 45 minutes, 300 mL of ethyl acetate was added to extract the organic phase; the organic phase was washed three times with NaOH aqueous solution (1 mol/L), twice with water, and once with brine; the crude product was concentrated and chromatographed on silica gel (ethyl acetate/petroleum ether: 1/1) to give 4-O-[(2,3,4,6-tetra-O-acetyl)-β-D-glucosyl]-5-methyl-2-(1-methylethylidene)-3(2H)-furanone as a white solid (0.97 g, 20% yield, compound I-2). $^1$H NMR (400 MHz, CDCl$_3$) δ (ppm): 5.24-5.07 (m, 4H), 4.20 (br d, J=12.3 Hz, 1H), 4.11 (br d, J=12.2 Hz, 1H), 3.68 (m, 1H), 2.25 (s, 3H), 2.19 (s, 3H), 2.11 (s, 3H), 2.04 (s, 3H), 1.99 (s, 6H), 1.97 (s, 3H). $^{13}$C NMR (100 MHz, CDCl$_3$) δ (ppm): 179.24, 170.67, 170.21, 170.01, 169.63, 168.30, 143.18, 135.65, 133.01, 99.75, 72.78, 72.01, 71.23, 68.52, 61.82, 20.94, 20.80, 20.74, 19.52, 17.25, 12.62. ESI-MS: 485 [M+1]$^+$.

Cultivation of single crystal: Compound I-2 (10 mg) was dissolved in anhydrous methanol (10 mL), water (4 mL) was added. After filtered, the filtrate was transferred to a 100 mL single-neck conical flask, and allowed to stand at 0-4° C. for 1-3 days. The single crystal was precipitated and collected for single crystal X-ray diffraction.

The configuration of compound I-2 was determined by crystal X-ray diffraction, the crystal form of compound I-2 was as described in the contents of the present invention, and the crystal structure of compound I-2 was shown in FIG. 1.

Step 3: 4-O-[(2,3,4,6-tetra-O-acetyl)-β-D-glucosyl]-5-methyl-2-(1-methylethylidene)-3(2H)-furanone (4.69 g, 10 mmol) was dissolved in 100 mL of methanol and sodium carbonate (5.3 g, 50 mmol) was added. After stirring for 4 h at room temperature, the crude product was concentrated after filtration and chromatographed on a C$_{18}$-bonded silica gel (methanol, 50% (v/v) aqueous solution) to give Phoenicein [4-O-β-D-glucosyl-5-methyl-2-(1-methylethylidene)-3(2H)-furanone] as an off-white solid (1.90 g, 60% yield, Compound I-1). $^1$H NMR (400 MHz, CD$_3$OD) δ (ppm): 4.74 (d, J=7.8 Hz, 1H), 3.84 (dd, J=12.0, 2.1 Hz, 1H), 3.69 (dd, J=12.0, 5.1 Hz, 1H), 3.45-3.27 (m, 4H), 2.35 (s, 3H), 2.30 (s, 3H), 2.05 (s, 3H). ESI-MS: 317 [M+1]$^+$.

Example 2

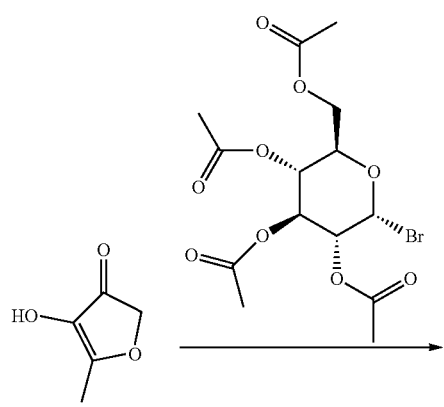

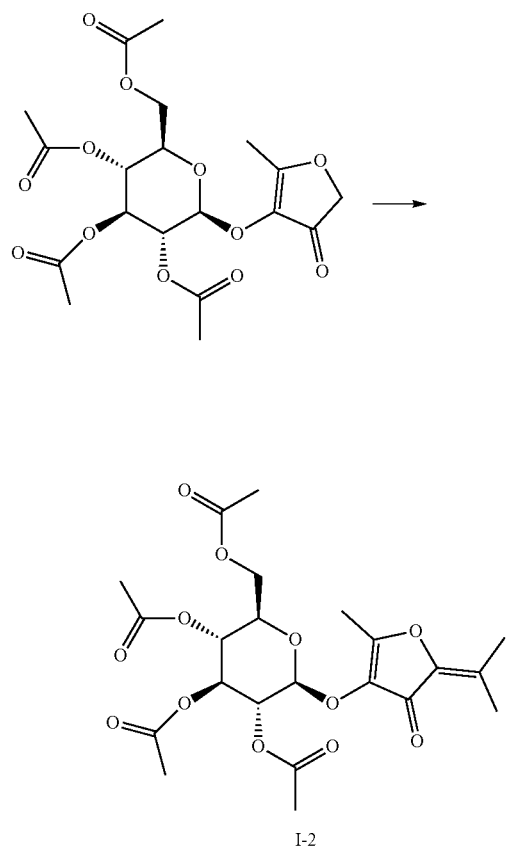

I-2

Step 1: 4-Hydroxy-5-methyl-3(2H)-furanone (1.14 g, 10 mmol, CAS: 19322-27-1), 2,3,4,6-tetra-O-acetyl-α-D-glucopyranosyl bromide (8.2 g, 20 mmol, CAS: 572-09-8), and tetrabutylammonium bromide (4.83 g, 15 mmol, CAS: 1643-19-2) were dissolved in 60 mL of dichloromethane and heated to 35° C.; 80 mL of aqueous NaOH (1 mol/L) was further added. After stirring for 45 minutes, 300 mL of ethyl acetate was added to extract the organic phase; the organic phase was washed three times with aqueous NaOH (1 mol/L), twice with water and once with brine; the crude product was concentrated and chromatographed on silica gel (ethyl acetate/petroleum ether: 1/1) to give 4-O-[(2,3,4,6-tetra-O-acetyl)-β-D-glucosyl]-5-methyl-3(2H)-furanone as a white solid (0.67 g, 15% yield). $^1$H NMR (400 MHz, CDCl$_3$) δ 5.24 (m, 1H), 5.12 (m, 3H), 4.48 (s, 2H), 4.23 (dd, J=12.2, 3.5 Hz, 1H), 4.15 (dd, J=12.5, 1.9 Hz, 1H), 3.72 (m, 1H), 2.24 (s, 3H), 2.12 (s, 3H), 2.07 (s, 3H), 2.02 (s, 6H). ESI-MS: 445 [M+1]$^+$.

Step 2: 4-O-[(2,3,4,6-tetra-O-acetyl)-β-D-glucosyl]-5-methyl-3(2H)-furanone (4.44 g, 10 mmol), copper acetate (905 mg, 5 mmol), and sodium acetate (680 mg, 5 mmol) were dissolved in 10 mL acetone and 30 mL glacial acetic acid, heated to 50° C., stirred and refluxed for 1 hour; then diluted with 150 mL of water, and extracted with 100 mL of petroleum ether; the crude product was concentrated and chromatographed on silica gel (ethyl acetate/petroleum ether: 1/1) to give 4-O-[(2,3,4,6-tetra-O-acetyl)-β-D-glucosyl]-5-methyl-2-(1-methylethylidene)-3(2H)-furanone as a white solid (1.94 g, 40% yield, Compound I-2).

Example 3

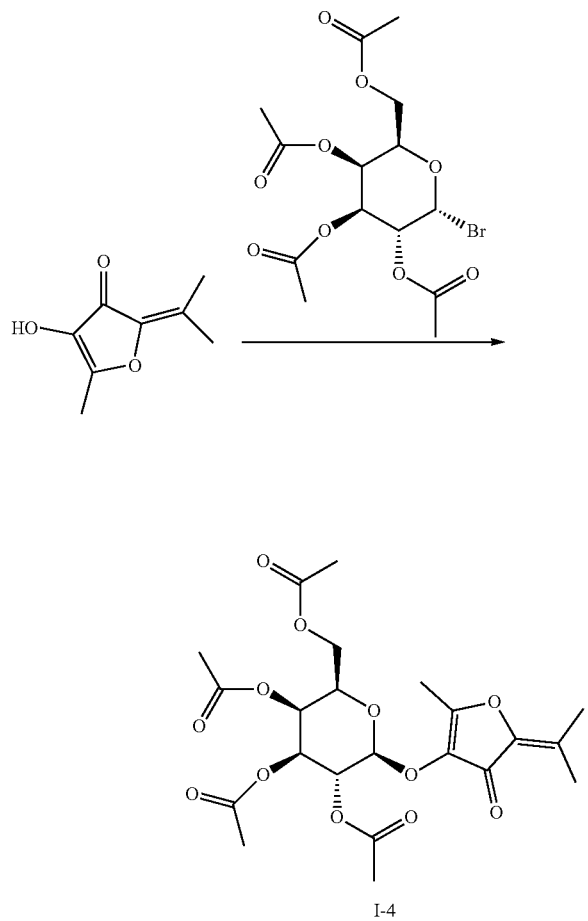

I-4

4-Hydroxy-5-methyl-2-(1-methylethylidene)-3(2H)-furanone (1.54 g, 10 mmol), 2,3,4,6-tetra-O-acetyl-α-D-galactopyranosyl bromide (6.15 g, 15 mmol), and tetrabutylammonium bromide (4.83 g, 15 mmol, CAS: 1643-19-2) were dissolved in 60 mL of dichloromethane and heated to 35° C.; 75 mL of NaOH aqueous solution (1 mol/L) was further added. After stirring for 45 minutes, 300 mL of ethyl acetate was added to extract the organic phase; the organic phase was washed three times with NaOH aqueous solution (1 mol/L), twice with water, and once with brine; the crude product was concentrated and chromatographed on silica gel (ethyl acetate/petroleum ether: 1/1) to give 4-O-[(2,3,4,6-tetra-O-acetyl)-β-D-galactosyl]-5-methyl-2-(1-methylethylidene)-3(2H)-furanone as a white solid (2.31 g, 48% yield, compound I-4).

I-4: $^1$H NMR (400 MHz, CDCl$_3$): δ 5.40 (d, J=2.7 Hz, 1H), 5.33 (dd, J=10.5, 8.0 Hz, 1H), 5.08 (d, J=8.0 Hz, 1H), 5.04 (dd, J=10.5, 3.5 Hz, 1H), 4.11 (m, 2H), 3.89 (t, J=6.7 Hz, 1H), 2.27 (s, 3H), 2.22 (s, 3H), 2.16 (s, 3H), 2.15 (s, 3H), 2.01 (s, 3H), 1.99 (s, 6H). $^{13}$C NMR (100 MHz, CDCl$_3$): δ 179.36, 170.47, 170.38, 170.27, 170.15, 168.42, 143.18, 135.94, 132.99, 100.72, 71.02, 70.85, 68.74, 67.01, 61.15, 21.08, 20.81, 20.76, 20.71, 19.51, 17.25, 12.70. ESI-MS: 485 [M+1]$^+$.

Example 4

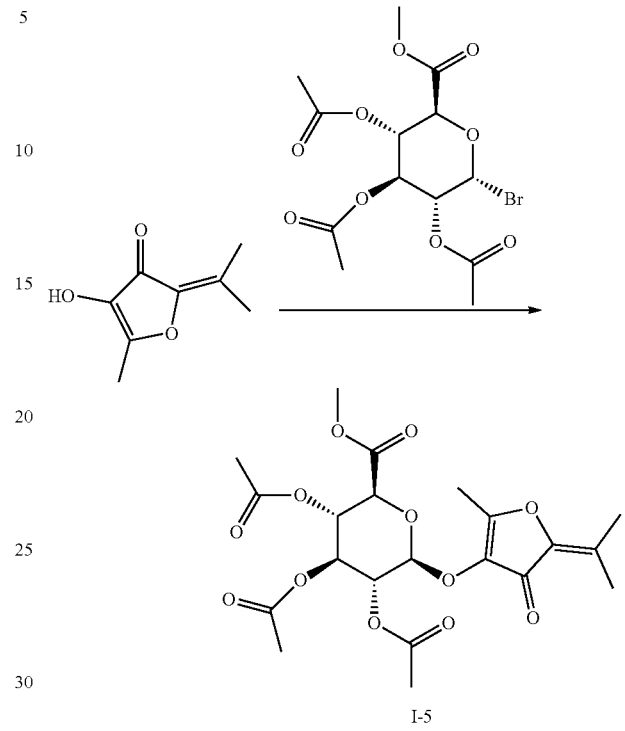

I-5

Compound I-5 was prepared using a similar method to example 3.

I-5: $^1$H NMR (400 MHz, CDCl$_3$) δ 5.31 (d, J=9.3 Hz, 1H), 5.27 (t, J=7.9 Hz, 1H), 5.21 (t, J=9.6 Hz, 1H), 5.16 (dd, J=9.2, 7.9 Hz, 1H), 4.02 (d, J=9.8 Hz, 1H), 3.72 (s, 3H), 2.26 (s, 3H), 2.24 (s, 3H), 2.12 (s, 3H), 2.02 (s, 3H), 2.01 (s, 3H), 1.98 (s, 3H). $^{13}$C NMR (100 MHz, CDCl$_3$) δ 179.18, 170.02, 169.91, 169.66, 168.75, 167.12, 143.20, 135.39, 133.25, 99.40, 72.41, 72.00, 71.01, 69.54, 52.95, 20.90, 20.73, 20.62, 19.53, 17.26, 12.70. ESI-MS: 471 [M+1]$^+$.

Example 5

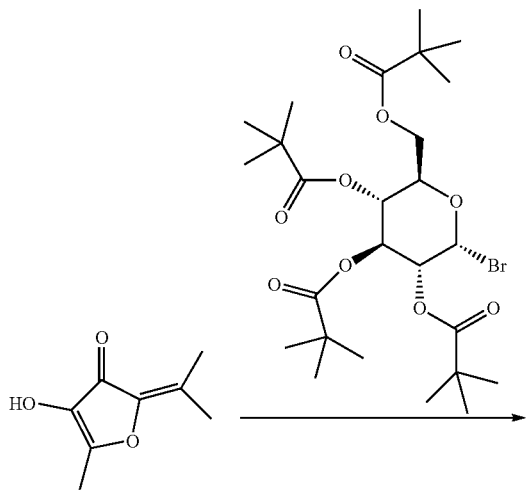

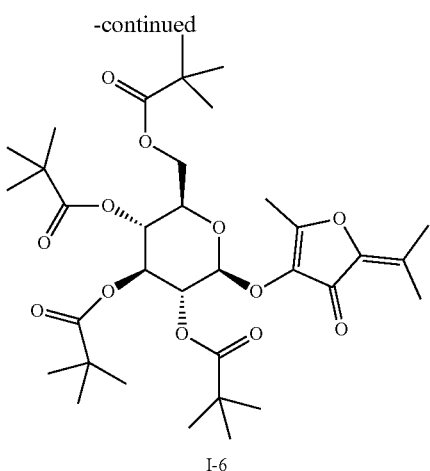

I-6

Compound I-6 was prepared using a similar method to example 3.

I-6: $^1$H NMR (400 MHz, CDCl$_3$) δ 5.34 (t, J=8.0 Hz, 1H), 5.30 (d, J=8.0 Hz, 1H), 5.16 (t, J=8.0 Hz, 1H), 5.14 (m, 1H), 4.17 (dd, J=12.2, 1.7 Hz, 1H), 4.02 (dd, J=12.3, 5.5 Hz, 1H), 3.70 (ddd, J=10.0, 5.4, 1.7 Hz, 1H), 2.25 (s, 3H), 2.18 (s, 3H), 1.97 (s, 3H), 1.19 (s, 9H), 1.16 (s, 9H), 1.14 (s, 9H), 1.12 (s, 9H). $^{13}$C NMR (100 MHz, CDCl$_3$) δ 179.05, 178.03, 177.20, 177.17, 176.66, 168.60, 143.19, 135.02, 132.56, 99.03, 72.43, 72.22, 71.25, 68.01, 61.69, 38.99, 38.93, 38.92, 38.85, 27.28(×3), 27.22(×3), 27.18(×3), 27.12(×3), 19.44, 17.23, 12.60. ESI-MS: 653 [M+1]$^+$.

Example 6

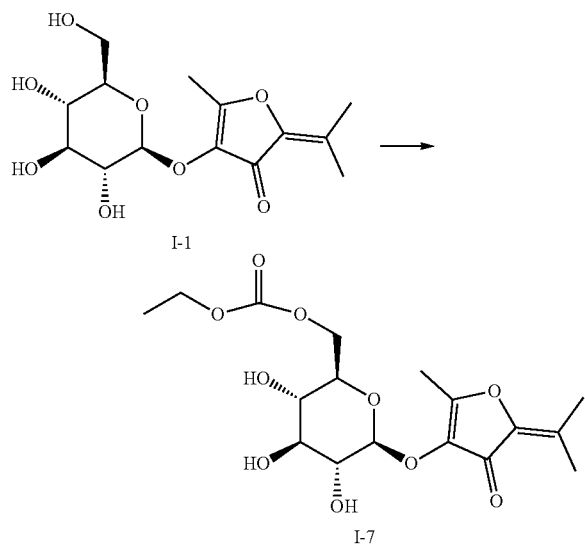

I-1 (316 mg, 1 mmol) was dissolved in toluene-ethanol (4:1, 30 mL) solution, Sc(OTF)3 (7.38 mg, 0.015 mmol) and DEPC (186 mg, 1.15 mmol) were added. The solution was heated to 50° C. for 2 h, then quenched with dilute acetic acid (2.5%, 3.75 mL). The mixture was cooled to 20° C. and the aqueous layer was discarded, the organic layer was washed again with dilute acetic acid (2.5%, 3.75 mL), and the aqueous layer was discarded. The final organic layer was then concentrated and chromatographed on silica gel (dichloromethane/methanol: 10/1) to give compound I-7 (210 mg, 54% yield).

I-7: $^1$H NMR (400 MHz, CDCl$_3$) δ 4.70 (d, J=8.1 Hz, 1H), 4.44 (d, J=11.0 Hz, 1H), 4.32 (dd, J=11.7, 5.7 Hz, 1H), 4.17 (m, 2H), 3.70-3.51 (m, 2H), 3.41 (t, J=9.3 Hz, 1H), 3.29 (t, J=8.6 Hz, 1H), 2.27 (s, 3H), 2.24 (s, 3H), 2.05 (s, 3H), 1.29 (t, J=7.1 Hz, 3H). $^{13}$C NMR (100 MHz, CDCl$_3$) δ 181.73, 171.69, 155.41, 143.22, 136.00, 134.72, 103.13, 75.81, 74.40, 72.07, 69.77, 66.73, 64.34, 19.73, 17.70, 14.37, 13.11. ESI-MS: 389 [M+1]$^+$.

Example 7

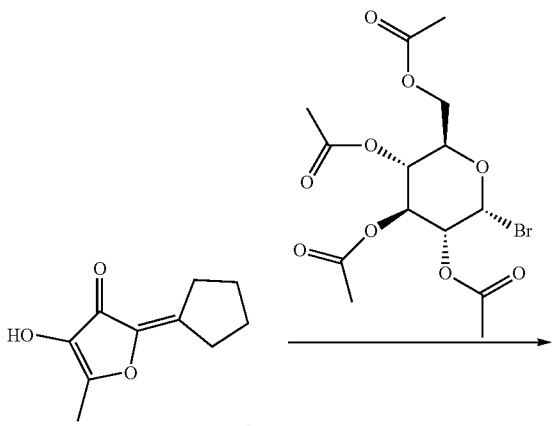

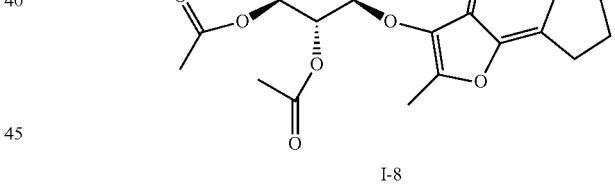

I-8

4-Hydroxy-5-methyl-2-cyclopentyl-3(2H)-furanone (1.80 g, 10 mmol), 2,3,4,6-tetra-0-acetyl-α-D-glucopyranosyl bromide (6.15 g, 15 mmol, CAS: 572-09-8), and tetrabutylammonium bromide (4.83 g, 15 mmol, CAS: 1643-19-2) were dissolved in 60 mL of dichloromethane and heated to 35° C.; 75 mL of NaOH aqueous solution (1 mol/L) was further added. After stirring for 45 minutes, 300 mL of ethyl acetate was added to extract the organic phase; the organic phase was washed three times with NaOH aqueous solution (1 mol/L), twice with water, and once with brine; the crude product was concentrated and chromatographed on silica gel (ethyl acetate/petroleum ether: 1/1) to give 4-O-[(2,3,4,6-tetra-O-acetyl)-β-D-glucosyl]-5-methyl-2-cyclopentyl-3 (2H)-furanone as a white solid (2.51 g, 49% yield, compound I-8).

I-8: $^1$H NMR (400 MHz, CDCl$_3$): δ 5.21-5.26 (m, 2H), 5.10-5.17 (m, 2H), 4.23 (dd, J=12.4, 4.4 Hz, 1H), 4.14 (dd, J=12.4, 2.4 Hz, 1H), 3.70 (m, 1H), 2.84 (t, J=6.6 Hz, 2H), 2.61 (t, J=7.2 Hz, 2H), 2.22 (s, 3H), 2.13 (s, 3H), 2.07 (s,

3H), 2.03 (s, 3H), 2.02 (s, 3H), 1.80 (m, 4H). $^{13}$C NMR (100 MHz, CDCl$_3$) δ 178.81, 170.69, 170.22, 170.02, 169.64, 168.68, 143.01, 140.87, 135.46, 99.68, 72.76, 71.95, 71.19, 68.45, 61.77, 31.05, 30.24, 26.80, 25.43, 20.96, 20.83, 20.75(×2), 12.72. ESI-MS: 511 [M+1]$^+$.

Example 8

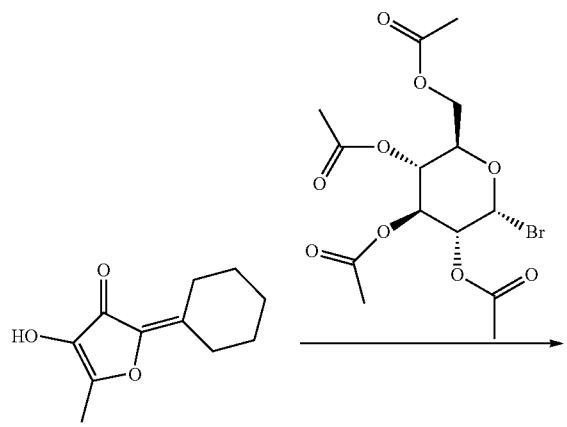

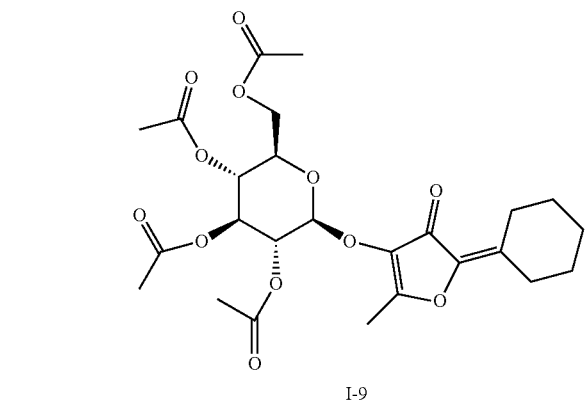

I-9

Compound I-9 was prepared using a similar method to example 7.

I-9: $^1$H NMR (400 MHz, CDCl$_3$) δ 5.23 (t, J=8.5 Hz, 1H), 5.19-5.05 (m, 3H), 4.22 (dd, J=12.4, 7.6 Hz, 1H), 4.14 (dd, J=12.4, 2.4 Hz, 1H), 3.69 (m, 1H), 2.94 (t, J=5.8 Hz, 2H), 2.43 (t, J=6.0 Hz, 2H), 2.20 (s, 3H), 2.13 (s, 3H), 2.06 (s, 3H), 2.02 (s, 6H), 1.66 (m, 6H). $^{13}$C NMR (100 MHz, CDCl$_3$) δ 179.80, 170.69, 170.23, 170.04, 169.65, 168.42, 140.96, 140.61, 135.83, 99.85, 72.73, 71.94, 71.18, 68.48, 61.79, 28.69, 27.87, 27.61, 26.27, 26.12, 20.97, 20.83, 20.76(×2), 12.66. ESI-MS: 525 [M+1]$^+$.

Example 9

I-10

Compound I-10 was prepared using a similar method to example 7.

I-10: $^1$H NMR (400 MHz, CDCl$_3$): δ 5.24 (t, J=6.4 Hz, 1H), 5.13 (m, 3H), 4.21 (dd, J=12.4, 5.6 Hz, 1H), 4.15 (dd, J=12.0, 2.4 Hz, 1H), 3.80 (m, 4H), 3.69 (m, 1H), 3.11 (m, 2H), 2.58 (t, J=5.6 Hz, 2H), 2.22 (s, 3H), 2.13 (s, 3H), 2.07 (s, 3H), 2.03 (s, 3H), 2.02 (s, 3H). $^{13}$C NMR (100 MHz, CDCl$_3$) δ 179.82, 170.65, 170.22, 169.98, 169.62, 169.15, 140.89, 135.80, 133.88, 99.86, 72.68, 72.00, 71.15, 68.55, 68.43, 68.10, 61.75, 28.91, 26.93, 20.94, 20.83, 20.75(×2), 12.72. ESI-MS: 527 [M+1]$^+$.

Example 10

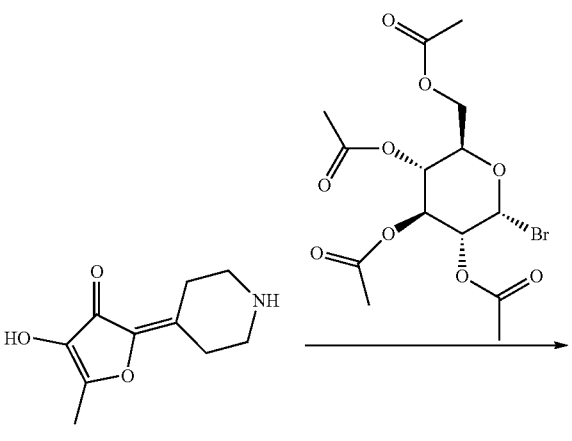

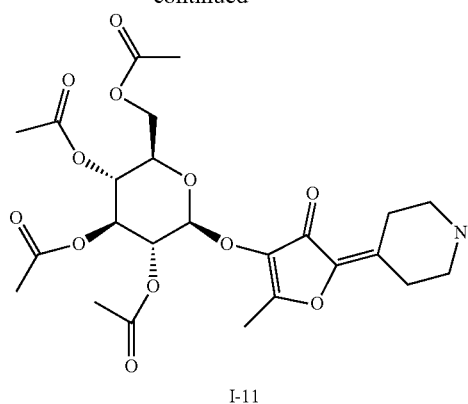

I-11

Compound I-11 was prepared using a similar method to example 7.

I-11: $^1$H NMR (400 MHz, CDCl$_3$) δ 9.81 (s, N—H), 5.24 (t, J=8.9 Hz, 1H), 5.13 (m, 3H), 4.19 (m, 2H), 3.70 (m, 1H), 3.52-3.16 (m, 6H), 2.91 (br s, 2H), 2.24 (s, 3H), 2.12 (s, 3H), 2.07 (s, 3H), 2.02 (s, 3H), 2.01 (s, 3H). $^{13}$C NMR (100 MHz, CDCl$_3$) δ 179.79, 170.65, 170.55, 170.23, 169.92, 169.61, 141.48, 135.77, 126.60, 99.94, 72.60, 72.08, 71.10, 68.32, 61.68, 44.43(×2), 24.25, 21.85, 20.93, 20.87, 20.75(×2), 12.85. ESI-MS: 526 [M+1]$^+$.

Example 11

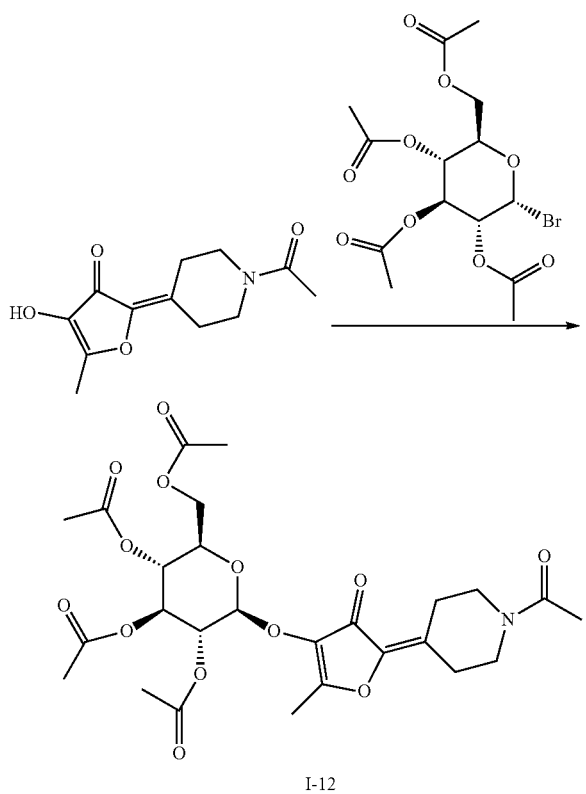

I-12

Compound I-12 was prepared using a similar method to example 7.

I-12: $^1$H NMR (400 MHz, CDCl$_3$): δ 5.10-5.27 (m, 4H), 4.11-4.25 (m, 2H), 3.73 (m, 4H), 3.56 (m, 1H), 3.10 (m, 2H), 2.58 (m, 2H), 2.24 (s, 3H), 2.15 (s, 3H), 2.13 (s, 3H), 2.07 (s, 3H), 2.03 (s, 3H), 2.02 (s, 3H). ESI-MS: 568 [M+1]$^+$.

Effect Example 1: Therapeutic Effect of Compound I-1 on Ulcerative Colitis

1. Experimental Procedure 1.1 Experimental Animals and Experimental Conditions

Thirty 10-week-old male C57 mice, SPF class animal house, temperature 20-26° C., humidity 40%-70%, alternating light-dark periods (12 h/12 h).

1.2 Grouping and Administration

Quarantine-qualified animals with similar weights were selected for the experiment. The mice were randomly grouped according to their weights, with five mice in each group, as shown in Table 1:

TABLE 1

| Group | Administration | Dosage (mg/kg) | Solvent |
| --- | --- | --- | --- |
| 1 Blank control group | intraperitoneal injection | 0 | sterile water |
| 2 Ulcerative colitis model group (dextran sodium sulphate) | intraperitoneal injection | 0 | sterile water |
| 3 Positive control group (cyclosporine A) | intramuscular injection | 50 | olive oil |
| 4 Low-dose treatment group (Compound I-1) | intraperitoneal injection | 10 | sterile water |
| 5 Middle-dose treatment group (Compound I-1) | intraperitoneal injection | 20 | sterile water |
| 6 High-dose treatment group (Compound I-1) | intraperitoneal injection | 40 | sterile water |

1.3 Experimental Method

Mice in the blank control group were given normal drinking water throughout the experiment. The other 5 groups of mice were given drinking water containing 2% dextran sodium sulphate (DSS) from day 1 to day 5, normal drinking water from day 6 to day 7, drinking water containing 2% dextran sodium sulphate from day 8 to day 12, and normal drinking water from day 13 to day 14. The experiment ended on day 14.

Animals in the blank control group and ulcerative colitis model group were given sterile water intraperitoneally from day 1, once a day; the other 4 groups were administered according to table 1, once a day, until the end of the experiment on day 14. Two hours after the first day of administration, the mice were started to drink water containing dextran sodium sulphate.

1.4 Measurement and Tissue Collection (1) The mice were weighed daily.

(2) Blood samples were collected from the orbital vein on day 14 and stored at −80° C.

(3) On day 14, the mice were sacrificed by cervical vertebra dislocation, the colon was removed and a small amount of fecal was taken from the colon and left as a sample. The colon length and colon weight were measured. A portion of the colon and the fecal sample was stored at −80° C.

2. Experimental Results

As shown in Tables 2 and 3, the weight of the mice in the ulcerative colitis model group was significantly reduced to 74.18% of the initial body weight compared to the blank control group, and compound I-1 had a significant ameliorating effect on the reduction in the weight of mice and showed a dose-dependent enhancement.

TABLE 2

| Group | Blank control group | Ulcerative colitis model group | Positive control group | Low-dose treatment group | Middle-dose treatment group | High-dose treatment group |
|---|---|---|---|---|---|---|
| Day 1/g | 27.9 | 27.8 | 27.8 | 27.9 | 27.8 | 27.6 |
| Day 2/g | 27.9 | 27.7 | 27.7 | 28.1 | 27.8 | 27.6 |
| Day 3/g | 28.0 | 27.6 | 27.7 | 28.0 | 27.9 | 27.6 |
| Day 4/g | 28.0 | 27.6 | 27.7 | 28.0 | 27.9 | 27.6 |
| Day 5/g | 28.1 | 26.7 | 27.4 | 27.2 | 27.5 | 27.3 |
| Day 6/g | 28.1 | 25.8 | 27.4 | 26.3 | 27.2 | 27.2 |
| Day 7/g | 28.1 | 24.8 | 27.3 | 25.9 | 26.7 | 26.8 |
| Day 8/g | 28.1 | 23.9 | 27.3 | 25.6 | 26.2 | 26.3 |
| Day 9/g | 28.1 | 22.8 | 27.2 | 25.3 | 25.9 | 25.8 |
| Day 10/g | 28.4 | 22.1 | 27.1 | 24.9 | 25.6 | 25.6 |
| Day 11/g | 28.5 | 21.7 | 26.9 | 24.4 | 25.3 | 25.5 |
| Day 12/g | 28.6 | 21.4 | 26.7 | 24.1 | 25.0 | 25.4 |
| Day 13/g | 28.7 | 21.0 | 26.6 | 23.8 | 24.8 | 25.3 |
| Day 14/g | 28.7 | 20.7 | 26.6 | 23.7 | 24.7 | 25.2 |

TABLE 3

Rate of change in weight of mice in each group

| Group | Blank control group | Ulcerative colitis model group | Positive control group | Low-dose treatment group | Middle-dose treatment group | High-dose treatment group |
|---|---|---|---|---|---|---|
| Day 1/% | 100.0 | 100.0 | 100.0 | 100.0 | 100.0 | 100.0 |
| Day 2/% | 100.2 | 99.5 | 99.6 | 100.6 | 100.1 | 99.9 |
| Day 3/% | 100.4 | 99.1 | 99.4 | 100.5 | 100.3 | 100.0 |
| Day 4/% | 100.4 | 99.1 | 99.4 | 100.3 | 100.3 | 100.0 |
| Day 5/% | 100.6 | 96.1 | 98.5 | 97.6 | 99.1 | 99.1 |
| Day 6/% | 100.6 | 92.9 | 98.3 | 94.3 | 97.8 | 98.7 |
| Day 7/% | 100.9 | 89.1 | 98.3 | 93.0 | 96.0 | 97.0 |
| Day 8/% | 100.9 | 85.8 | 98.1 | 91.6 | 94.3 | 95.3 |
| Day 9/% | 100.9 | 82.0 | 97.9 | 90.8 | 93.2 | 93.5 |
| Day 10/% | 102.0 | 79.6 | 97.3 | 89.1 | 92.2 | 92.7 |
| Day 11/% | 102.4 | 78.1 | 96.8 | 87.5 | 91.1 | 92.2 |
| Day 12/% | 102.7 | 76.8 | 96.0 | 86.4 | 90.0 | 92.0 |
| Day 13/% | 102.9 | 75.6 | 95.6 | 85.3 | 89.2 | 91.5 |
| Day 14/% | 102.9 | 74.3 | 95.5 | 84.9 | 88.8 | 91.4 |

As shown in Table 4, compared with the blank control group, the colon length of mice in the ulcerative colitis model group was significantly shortened, and the average length was shortened from 7.18 cm to 5.02 cm. The administration of compound I-1 could gradually restore the length of the colon to normal and showed a dose-dependent effect, the high-dose treatment group was even better than the positive control group.

TABLE 4

| Group | Blank control group | Ulcerative colitis model group | Positive control group | Low-dose treatment group | Middle-dose treatment group | High-dose treatment group |
|---|---|---|---|---|---|---|
| Colon length/cm | 7.18 | 5.02 | 6.36 | 5.46 | 6.04 | 6.52 |

Average colon length of mice in each group

As shown in Table 5, compared with the blank control group, the colon weight of mice in the ulcerative colitis model group was significantly increased.

TABLE 5

| Group | Blank control group | Ulcerative colitis model group | Positive control group | Low-dose treatment group | Middle-dose treatment group | High-dose treatment group |
|---|---|---|---|---|---|---|
| Colon weight/g | 0.1786 | 0.2017 | 0.1840 | 0.1909 | 0.2115 | 0.2129 |

Average colon weight of mice in each group

As shown in Table 6, compared with the blank control group, the unit colon weight (colon weight/colon length) of mice in the ulcerative colitis model group was significantly increased. The administration of compound I-1 could significantly improve the unit colon weight, and the high-dose group showed the best performance.

TABLE 6

| Group | Blank control group | Ulcerative colitis model group | Positive control group | Low-dose treatment group | Middle-dose treatment group | High-dose treatment group |
|---|---|---|---|---|---|---|
| Unit colon weight (g/cm) | 0.0249 | 0.0395 | 0.0289 | 0.0351 | 0.0351 | 0.0327 |

Unit colon weight of mice in each group

Figure 2:
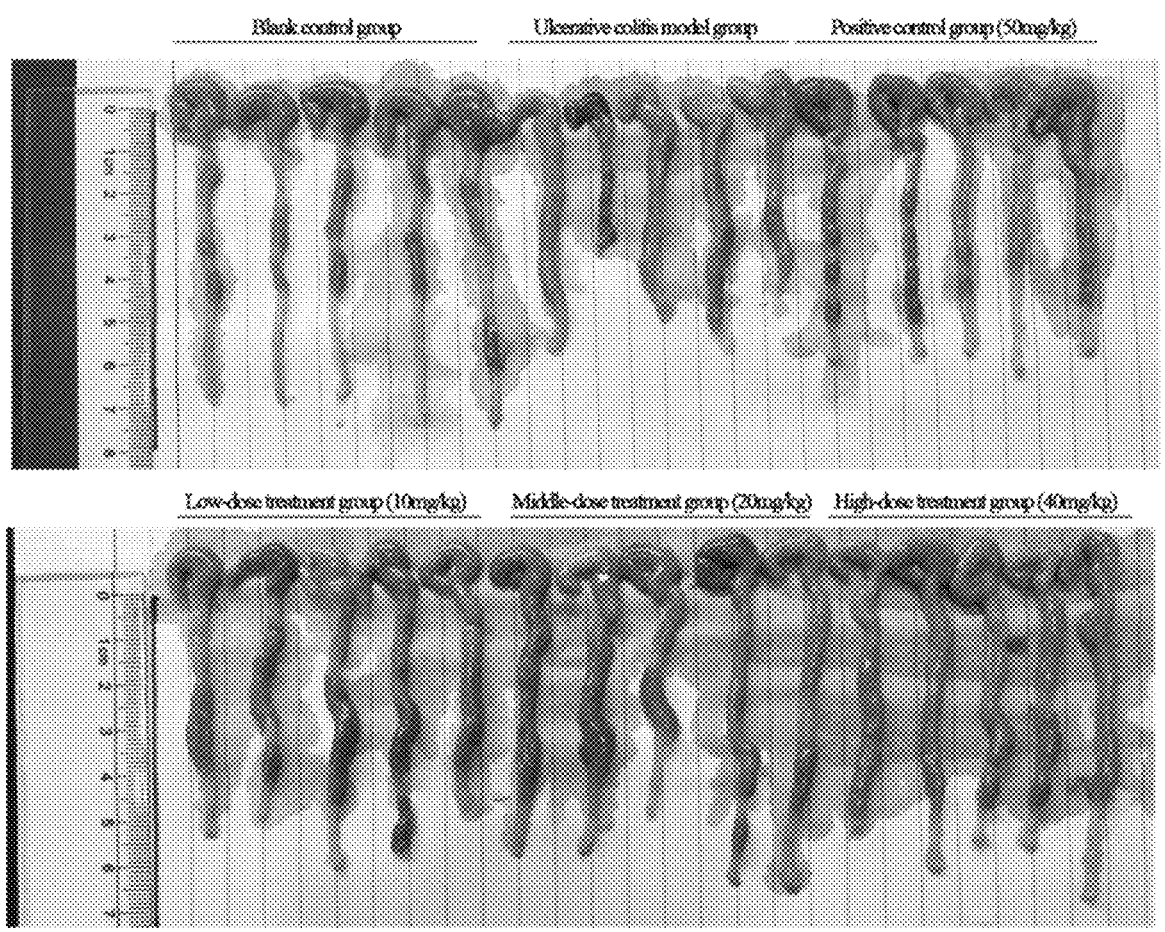
FIG. 2 is the colons morphology of the mice in each group in effect example 1.

As shown in Tables 2 to 6 and FIG. 2, after intraperitoneal administration of different concentrations, the reduction of weight and shortening of colon length of mice in the treatment groups were significantly relieved. Compared with the ulcerative colitis model group, the unit colon weight in the treatment groups showed a decreasing trend.

Effect example 2: Therapeutic effect of compound I-2, I-4, I-5, and I-6 on ulcerative colitis 1. Experimental Procedure 1.1 Experimental Animals and Experimental Conditions Thirty-five 10-week-old male C57 mice, SPF class animal house, temperature 20-26° C., humidity 40%-70%, alternating light-dark periods (12 h/12 h).

1.2 Grouping and Administration

Quarantine-qualified animals with similar weights were selected for the experiment. The mice were randomly grouped according to their weights, with five mice in each group, as shown in Table 7:

TABLE 7

| | Group | Administration | Dosage (mg/kg) | Solvent |
|---|---|---|---|---|
| 1 | Blank control group | oral gavage | 0 | sterile water |
| 2 | Ulcerative colitis model group (dextran sodium sulphate) | oral gavage | 0 | sterile water |
| 3 | Positive control group (SASP) | oral gavage | 30 | olive oil |
| 4 | Treatment group I-2 (compound I-2) | oral gavage | 40 | sterile water |
| 5 | Treatment group I-4 (compound I-4) | oral gavage | 40 | sterile water |
| 6 | Treatment group I-5 (compound I-5) | oral gavage | 40 | sterile water |
| 7 | Treatment group I-6 (compound I-6) | oral gavage | 40 | sterile water |

Mice in the blank control group were given normal drinking water throughout the experiment. The other 6 groups of mice were given drinking water containing 2% dextran sodium sulphate from day 1 to day 5, normal drinking water from day 6 to day 7, drinking water containing 2% dextran sodium sulphate from day 8 to day 12, and normal drinking water from day 13 to day 14. The experiment ended on day 14. All groups were administered by oral gavage once a day according to table 7, until the end of the experiment on day 14.

1.3 Measurement and Tissue Collection (1) The mice were weighed daily.

(2) Blood samples were collected from the orbital vein on day 14 and stored at −80° C.

(3) On day 14, the mice were sacrificed by cervical vertebra dislocation, the colon was removed and a small amount of fecal was taken from the colon and left as a sample. The colon length and colon weight were measured. A portion of the colon and the fecal sample was stored at −80° C.

2. Experimental Results

The experimental results are shown in Tables 8 to 9:

TABLE 8

Average weight of mice in each group

| Group | Blank control group | Ulcerative colitis model group | Positive control group | Treatment group I-2 | Treatment group I-4 | Treatment group I-5 | Treatment group I-6 |
|---|---|---|---|---|---|---|---|
| Day 1/g | 27.36 | 26.82 | 26.8 | 26.86 | 26.72 | 26.9 | 26.9 |
| Day 2/g | 27.44 | 26.88 | 26.86 | 26.9 | 26.76 | 26.92 | 26.94 |
| Day 3/g | 27.46 | 26.74 | 26.82 | 26.82 | 26.72 | 26.88 | 26.9 |
| Day 4/g | 27.36 | 26.76 | 26.8 | 26.86 | 26.72 | 26.9 | 26.9 |
| Day 5/g | 27.4 | 26.04 | 26.52 | 26.58 | 26.44 | 26.58 | 26.64 |
| Day 6/g | 27.36 | 25.44 | 25.74 | 26.48 | 26.36 | 26.32 | 26.2 |
| Day 7/g | 27.42 | 24.34 | 24.38 | 25.18 | 24.82 | 25.3 | 24.52 |
| Day 8/g | 27.52 | 23.44 | 22.92 | 23.78 | 23.44 | 23.6 | 24.38 |
| Day 9/g | 27.18 | 22.88 | 22.3 | 23.64 | 23.3 | 23.24 | 24.42 |
| Day 10/g | 27.4 | 22.28 | 22.34 | 23.64 | 23.3 | 23.24 | 24.42 |
| Day 11/g | 27.5 | 22.08 | 22.68 | 24.72 | 24.02 | 24.2 | 24.66 |
| Day 12/g | 27.66 | 22.2 | 23.14 | 24.82 | 24.14 | 24.48 | 24.94 |
| Day 13/g | 27.76 | 22.26 | 23.52 | 24.8 | 24.5 | 24.5 | 24.72 |
| Day 14/g | 27.76 | 22.18 | 23.52 | 24.92 | 24.68 | 24.68 | 24.5 |

TABLE 9

Average colon length of mice in each group

| Group | Blank control group | Ulcerative colitis model group | Positive control group | Treatment group I-2 | Treatment group I-4 | Treatment group I-5 | Treatment group I-6 |
|---|---|---|---|---|---|---|---|
| Colon length/cm | 7.1 | 5.8 | 6.0 | 6.2 | 6.2 | 6.0 | 5.9 |

The results showed that the weight of mice in the ulcerative colitis model group was significantly lower compared to the blank control group, and oral gavage administration of compounds I-2, I-4, I-5, and I-6 had a significant improvement in the reduction of weight in mice, and all of compounds I-2, I-4, I-5, and I-6 were better than the positive control drug salazosulfapyridine (SASP).

Effect Example 3: Therapeutic Effect of Compound I-1, I-2, and I-7 to I-12 on Ulcerative Colitis 1. Experimental Procedure 1.1 Experimental Animals and Experimental Conditions Fifty 10-week-old male C57 mice, SPF class animal house, temperature 20-26° C., humidity 40%-70%, alternating light-dark periods (12 h/12 h).

1.2 Grouping and Administration

Quarantine-qualified animals with similar weights were selected for the experiment. The mice were randomly grouped according to their weights, with five mice in each group, as shown in Table 10:

TABLE 10

| Group | Administration | Dosage (mg/kg) | Solvent |
|---|---|---|---|
| 1 Blank control group | oral gavage | 0 | sterile water |
| 2 Ulcerative colitis model group (dextran sodium sulphate) | oral gavage | 0 | sterile water |
| 3 Treatment group I-1 (compound I-1) | oral gavage | 40 | sterile water |

TABLE 10-continued

| Group | Administration | Dosage (mg/kg) | Solvent |
|---|---|---|---|
| 4 Treatment group I-2 (compound I-2) | oral gavage | 40 | sterile water |
| 5 Treatment group I-7 (compound I-7) | oral gavage | 40 | sterile water |
| 6 Treatment group I-8 (compound I-8) | oral gavage | 40 | sterile water |
| 7 Treatment group I-9 (compound I-9) | oral gavage | 40 | sterile water |
| 8 Treatment group I-10 (compound I-10) | oral gavage | 40 | sterile water |
| 9 Treatment group I-11 (compound I-11) | oral gavage | 40 | sterile water |
| 10 Treatment group I-12 (compound I-12) | oral gavage | 40 | sterile water |

Mice in the blank control group were given normal drinking water throughout the experiment. The other 9 groups of mice were given drinking water containing 2% dextran sodium sulphate from day 1 to day 7. All groups were administered by oral gavage once a day according to table 10, until the end of the experiment.

1.3 Measurement and Tissue Collection (1) The mice were weighed daily.

(2) Blood samples were collected from the orbital vein on day 7 and stored at −80° C.

(3) On day 7, the mice were sacrificed by cervical vertebra dislocation, the colon was removed and a small amount of fecal was taken from the colon and left as a sample. The colon length and colon weight were measured. A portion of the colon and the fecal sample was stored at −80° C.

2. Experimental Results

The experimental results are shown in Tables 11 to 12:

TABLE 11

Average weight of mice in each group

| Weight of mice | Day 1/g | Day 2/g | Day 3/g | Day 4/g | Day 5/g | Day 6/g | Day 7/g |
|---|---|---|---|---|---|---|---|
| Blank control group | 21.05 | 21.38 | 21.40 | 21.15 | 20.80 | 21.38 | 21.43 |
| Ulcerative colitis model group | 21.82 | 21.97 | 21.92 | 21.68 | 20.40 | 19.52 | 18.47 |
| Treatment group I-1 | 21.33 | 20.97 | 20.80 | 20.85 | 20.53 | 20.13 | 19.82 |
| Treatment group I-2 | 21.53 | 21.42 | 21.25 | 20.97 | 20.72 | 20.27 | 19.27 |
| Treatment group I-7 | 21.47 | 21.62 | 21.18 | 20.82 | 20.13 | 20.07 | 19.88 |
| Treatment group I-8 | 21.85 | 21.97 | 21.77 | 21.33 | 20.62 | 20.52 | 20.32 |
| Treatment group I-9 | 21.20 | 21.17 | 20.92 | 20.47 | 20.03 | 19.42 | 19.38 |
| Treatment group I-10 | 21.95 | 21.60 | 21.18 | 21.27 | 20.90 | 20.13 | 19.25 |
| Treatment group I-11 | 21.62 | 21.30 | 21.10 | 20.97 | 20.32 | 19.93 | 19.30 |
| Treatment group I-12 | 21.25 | 21.22 | 21.13 | 20.62 | 20.10 | 16.32 | 18.88 |

TABLE 12

Average colon length of mice in each group

| | Group | | | | | | | | | |
|---|---|---|---|---|---|---|---|---|---|---|
| | Blank control group | ulcerative colitis model group | Treatment group I-1 | Treatment group I-2 | Treatment group I-7 | Treatment group I-8 | Treatment group I-9 | Treatment group I-10 | Treatment group I-11 | Treatment group I-12 |
| Colon length/cm | 7.2 | 5.1 | 6.2 | 5.8 | 5.4 | 6.1 | 6.3 | 5.8 | 6.2 | 5.7 |

The results showed that the weight of mice in the ulcerative colitis model group was significantly lower compared to the blank control group; except for compound I-11, all the tested compounds by oral gavage administration had a significant improvement in the reduction of weight in mice. In addition, oral gavage administration of I-1, I-8, I-9, and I-11 can gradually restore the colon length.

Although the examples of the invention have been described herein, those skilled in the art should understand that the examples are merely illustrative, and various changes may be made to the examples without departing from the principle and spirit of the invention. Therefore, the scope of the invention is to be limited by the appended claims.

What is claimed is:

1. A compound represented by formula A-1, a pharmaceutically acceptable salt thereof, a solvate thereof, or a crystal form thereof,

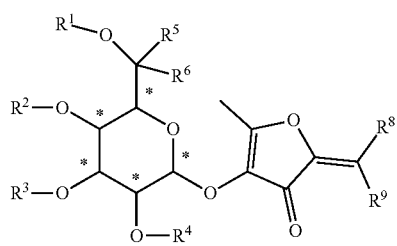

A-1 wherein $R^1$, $R^2$, $R^3$, and $R^4$ are independently hydrogen, $C_{1-4}$ alkyl, benzyl, —C(=O)R, or —C(=O)—O—R', and $R^1$, $R^2$, $R^3$, and $R^4$ are not simultaneously hydrogen;

each R' is independently $C_{1-4}$ alkyl;

each R is independently $C_{1-4}$ alkyl or phenyl;

$R^5$ and $R^6$ are independently hydrogen, or $R^5$ and $R^6$ are taken together to form =O;

$R^8$ and $R^9$ are independently $C_{1-4}$ alkyl;

alternatively, $R^8$ and $R^9$ are taken together with the carbon atom to which they are attached to form 3- to 7-membered cycloalkyl, 3- to 7-membered heterocycloalkyl, 3- to 7-membered cycloalkyl substituted with one or a plurality of $R^a$, or 3- to 7-membered heterocycloalkyl substituted with one or a plurality of $R^b$; in the 3- to 7-membered heterocycloalkyl and the 3- to 7-membered heterocycloalkyl substituted with one or a plurality of $R^b$, the heteroatoms in the 3- to 7-membered heterocycloalkyl are independently selected from N, O, and S, and the number of heteroatoms is independently 1, 2, or 3;

$R^a$ and $R^b$ are independently $C_{1-4}$ alkyl, —C(=O)R";

each R" is independently $C_{1-4}$ alkyl;

carbon atoms marked with "*" indicate that when the carbon atoms are chiral, the carbon atoms are in the R-configuration, S-configuration, or a mixture of R-configuration and S-configuration.

2. The compound represented by formula A-1, the pharmaceutically acceptable salt thereof, the solvate thereof, or the crystal form thereof as claimed in claim 1, wherein the structure of the compound represented by formula A-1 is as follows:

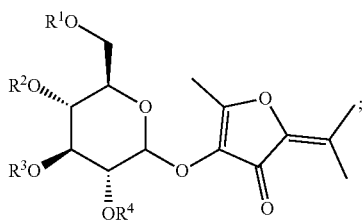

A

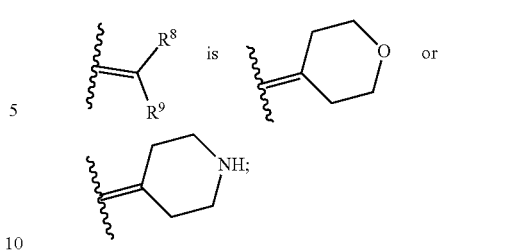

wherein $R^1$, $R^2$, $R^3$, and $R^4$ are independently hydrogen, $C_{1-4}$ alkyl, benzyl or —C(=O)R, and $R^1$, $R^2$, $R^3$, and $R^4$ are not simultaneously hydrogen;
each R is independently $C_{1-4}$ alkyl or phenyl.

3. The compound represented by formula A-1, the pharmaceutically acceptable salt thereof, the solvent thereof, or the crystal form thereof as claimed in claim 1, wherein when $R^1$, $R^2$, $R^3$, and $R^4$ are independently $C_{1-4}$ alkyl, then the $C_{1-4}$ alkyl is methyl, ethyl, n-propyl, isopropyl, n-butyl, isobutyl, sec-butyl, or tert-butyl;
  or, each R' is independently methyl, ethyl, n-propyl, isopropyl, n-butyl, isobutyl, sec-butyl, or tert-butyl;
  or, when each R is independently $C_{1-4}$ alkyl, then the $C_{1-4}$ alkyl is methyl, ethyl, n-propyl, isopropyl, n-butyl, isobutyl, sec-butyl, or tert-butyl;
  or, when $R^8$ and $R^9$ are independently $C_{1-4}$ alkyl, then the $C_{1-4}$ alkyl is methyl, ethyl, n-propyl, isopropyl, n-butyl, isobutyl, sec-butyl, or tert-butyl;
  or, when $R^8$ and $R^9$ are taken together with the carbon atom to which they are attached to form 3- to 7-membered cycloalkyl or 3- to 7-membered cycloalkyl substituted with one or a plurality of $R^a$, then the 3- to 7-membered cycloalkyl is a 5- to 6-membered cycloalkyl;
  or, when $R^8$ and $R^9$ are taken together with the carbon atom to which they are attached to form 3- to 7-membered heterocycloalkyl or 3- to 7-membered heterocycloalkyl substituted with one or a plurality of $R^b$, in the 3- to 7-membered heterocycloalkyl, the heteroatoms are independently selected from N and O, and the number of heteroatoms is independently 1;
  or, when $R^8$ and $R^9$ are taken together with the carbon atom to which they are attached to form 3- to 7-membered heterocycloalkyl or 3- to 7-membered heterocycloalkyl substituted with one or a plurality of $R^b$, then the 3- to 7-membered heterocycloalkyl is a 5- to 6-membered heterocycloalkyl;
  or, when $R^a$ and $R^b$ are independently $C_{1-4}$ alkyl, then the $C_{1-4}$ alkyl is methyl, ethyl, n-propyl, isopropyl, n-butyl, isobutyl, sec-butyl, or tert-butyl;
  or, each R'' is independently methyl, ethyl, n-propyl, isopropyl, n-butyl, isobutyl, sec-butyl, or tert-butyl.

4. The compound represented by formula A-1, the pharmaceutically acceptable salt thereof, the solvent thereof, or the crystal form thereof as claimed in claim 3, wherein when 10, $R^2$, $R^3$, and $R^4$ are independently $C_{1-4}$ alkyl, then the $C_{1-4}$ alkyl is methyl;
  or, each R' is independently ethyl;
  or, when each R is independently $C_{1-4}$ alkyl, then the $C_{1-4}$ alkyl is methyl or tert-butyl;
  or, when $R^8$ and $R^9$ are independently $C_{1-4}$ alkyl, then the $C_{1-4}$ alkyl is methyl;
  or, when $R^8$ and $R^9$ are taken together with the carbon atom to which they are attached to form 3- to 7-membered heterocycloalkyl, then or, each R'' is independently methyl;
  or, when $R^8$ and $R^9$ are taken together with the carbon atom to which they are attached to form 3- to 7-membered heterocycloalkyl substituted with one or a plurality of $R^b$, then

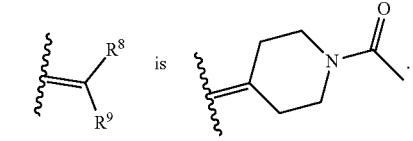

5. The compound represented by formula A-1, the pharmaceutically acceptable salt thereof, the solvent thereof, or the crystal form thereof as claimed in claim 1, wherein $R^1$, $R^2$, $R^3$, and $R^4$ are independently hydrogen, $C_{1-4}$ alkyl, —C(=O)R, or —C(=O)—O—R';
  or, each R is independently $C_{1-4}$ alkyl;
  or, $R^a$ and $R^b$ are independently —C(=O)R'';
  or, $R^8$ and $R^9$ are independently $C_{1-4}$ alkyl, or, $R^8$ and $R^9$ are taken together with the carbon atom to which they are attached to form 3- to 7-membered cycloalkyl, 3- to 7-membered heterocycloalkyl, or 3- to 7-membered heterocycloalkyl substituted with one or a plurality of $R^b$;
  or,

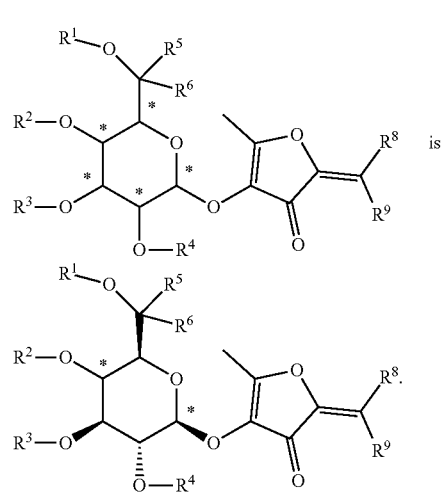

A-1

6. The compound represented by formula A-1, the pharmaceutically acceptable salt thereof, the solvate thereof, or the crystal form thereof as claimed in claim 5,
  wherein $R^1$ is $C_1$-4 alkyl, —C(=O)R, or —C(=O)—O—R';

or, when $R^5$ and $R^6$ are independently hydrogen, then $R^1$ is —C(=O)R or —C(=O)—O—R'; when $R^5$ and $R^6$ are taken together to form =O, then $R^1$ is $C_{1-4}$ alkyl;

or, $R^2$ and $R^3$ and $R^4$ are independently hydrogen or —C(=O)R;

or, each R is independently methyl or tert-butyl;

or, $R^a$ and $R^b$ are independently

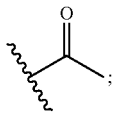

or, $R^8$ and $R^9$ are independently $C_{1-4}$ alkyl, or, $R^8$ and $R^9$ are taken together with the carbon atom to which they are attached to form 3- to 7-membered cycloalkyl or 3- to 7-membered heterocycloalkyl;

or,

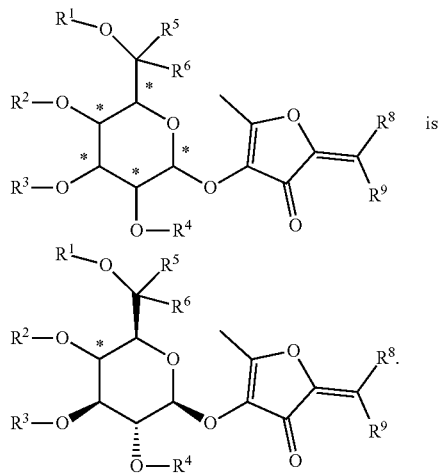

A-1

7. The compound represented by formula A-1, the pharmaceutically acceptable salt thereof, the solvate thereof, or the crystal form thereof as claimed in claim 5, wherein $R^1$ is methyl,

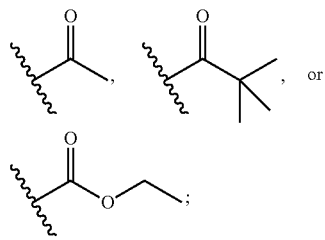

or, $R^2$, $R^3$, and $R^4$ are independently hydrogen,

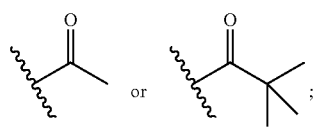

or, $R^2$, $R^3$, and $R^4$ are the same group;

or,

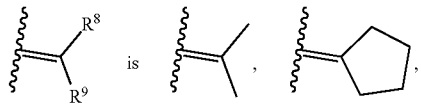

is

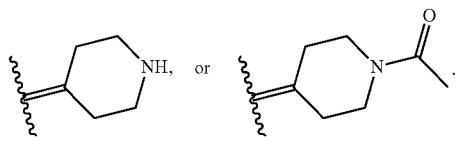

8. The compound represented by formula A-1, the pharmaceutically acceptable salt thereof, the solvate thereof, or the crystal form thereof as claimed in claim 2, wherein $R^1$, $R^2$, $R^3$, and $R^4$ are independently hydrogen or —C(=O)R;

or, each R is independently $C_{1-4}$ alkyl.

9. The compound represented by formula A-1, the pharmaceutically acceptable salt thereof, the solvate thereof, or the crystal form thereof as claimed in claim 2, wherein when $R^1$, $R^2$, $R^3$ and $R^4$ are independently $C_{1-4}$ alkyl, then the $C_{1-4}$ alkyl is methyl, ethyl, n-propyl, isopropyl, n-butyl, isobutyl, sec-butyl, or tert-butyl;

or, each R is independently methyl, ethyl, n-propyl, isopropyl, n-butyl, isobutyl, sec-butyl, tert-butyl, or phenyl;

or, $R^1$, $R^2$, $R^3$, and $R^4$ are the same group;

or, the structure of the said compound represented by formula A is as follows:

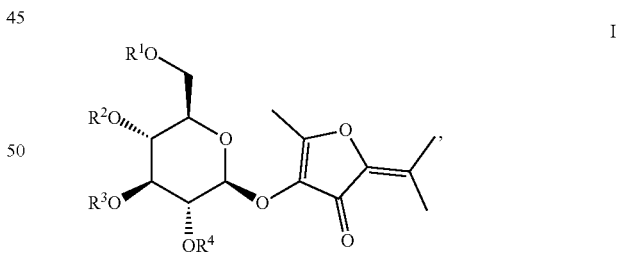

I

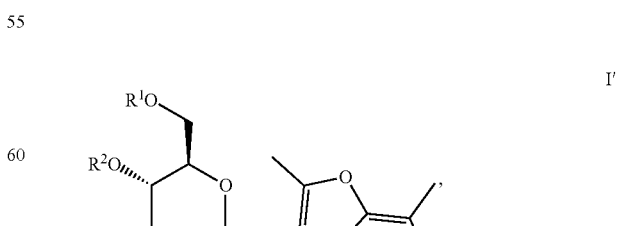

I'

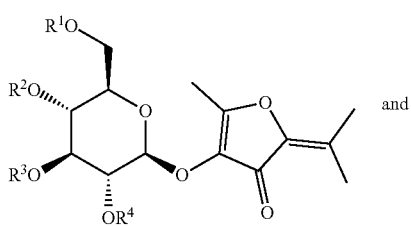
I
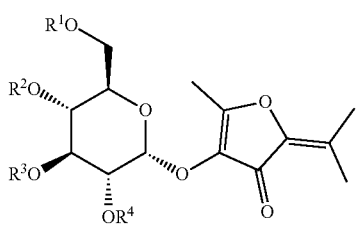
I'
in a molar ratio of 1:1.
10. The compound represented by formula A-1, the pharmaceutically acceptable salt thereof, the solvent thereof, or the crystal form thereof as claimed in claim 1, wherein the compound represented by formula A-1 is any of the following compounds,
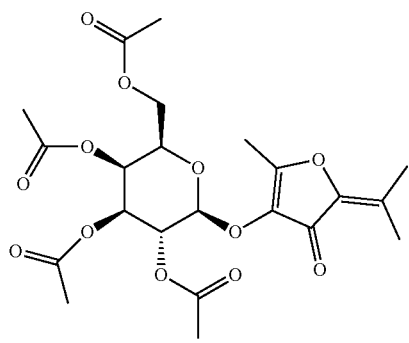
I-4
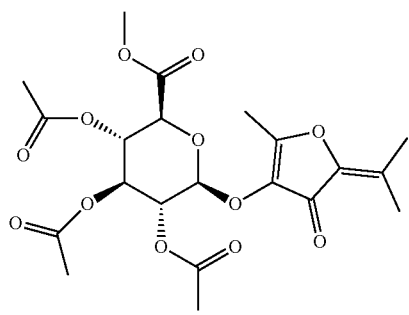
I-5
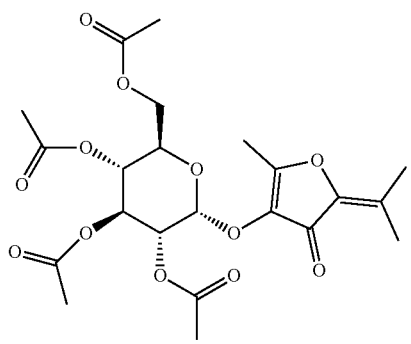
I-2
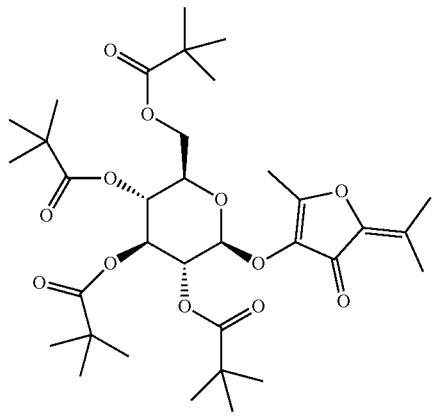
I-6
I'-2
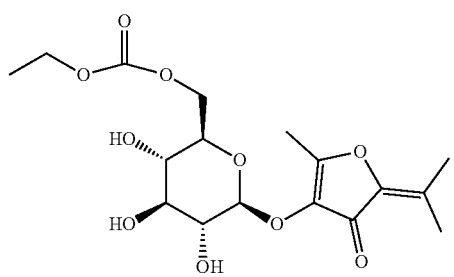
I-7

53
-continued

I-8
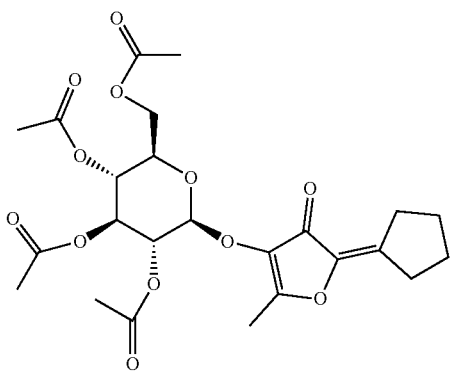

I-9
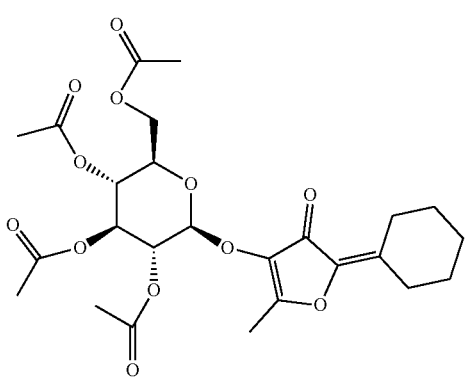

I-10
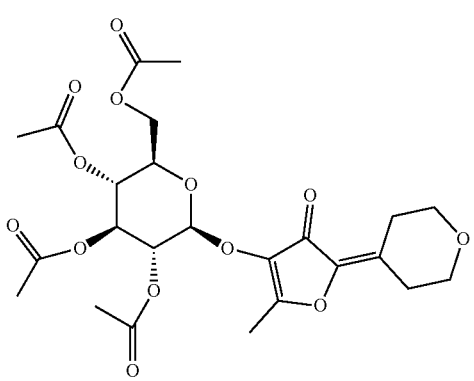

I-11
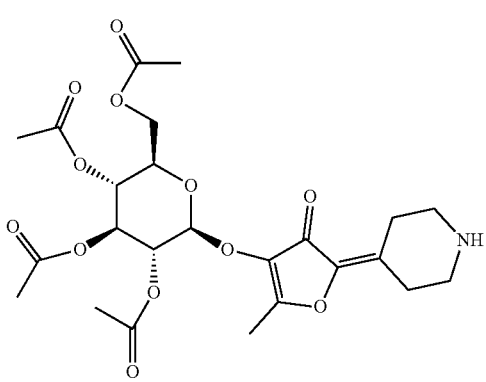

54
-continued

I-12
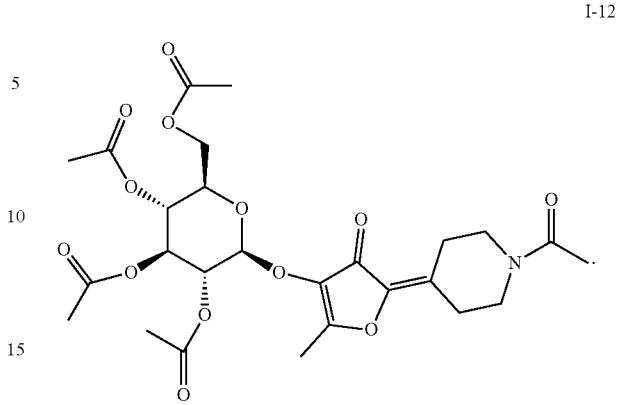

11. A pharmaceutical composition comprising a compound as represented by formula A-1, a pharmaceutically acceptable salt thereof, and a pharmaceutical adjuvant;

A-1
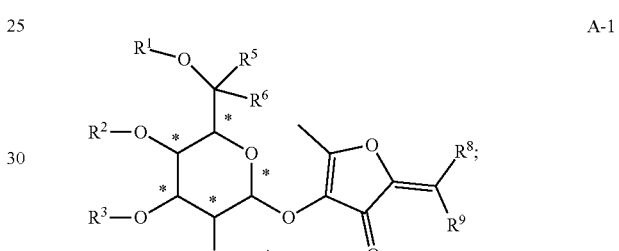

wherein $R^1$, $R^2$, $R^3$, and $R^4$ are independently hydrogen, $C_{1-4}$ alkyl, benzyl, —C(=O)R, or —C(=O)—O—R; R, R', *, $R^5$, $R^6$, $R^8$, and $R^9$ are defined as claimed in claim 1.

12. The pharmaceutical composition as claimed in claim 11, wherein the structure of the compound represented by formula A-1 is as follows:

A
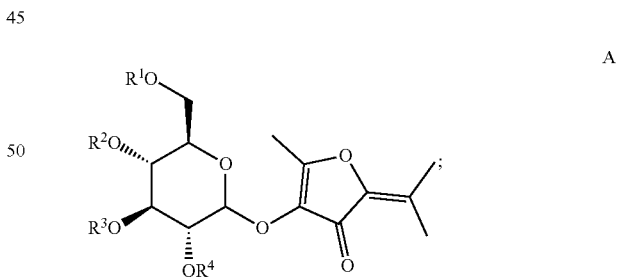

wherein $R^1$, $R^2$, $R^3$, and $R^4$ are independently hydrogen, $C_{1-4}$ alkyl, benzyl, —C(=O)R; R is defined as above.

13. The pharmaceutical composition as claimed in claim 11, wherein the pharmaceutical composition is a pharmaceutical composition for treating inflammatory bowel disease;

or, when $R^1$, $R^2$, $R^3$, and $R^4$ are independently $C_{1-4}$ alkyl, then the $C_{1-4}$ alkyl is methyl, ethyl, n-propyl, isopropyl, n-butyl, isobutyl, sec-butyl, or tert-butyl;

or, $R^1$, $R^2$, $R^3$, and $R^4$ are independently hydrogen, —C(=O)R, or —C(=O)—O—R';

or, $R^2$, $R^3$, and $R^4$ are the same group;

or,

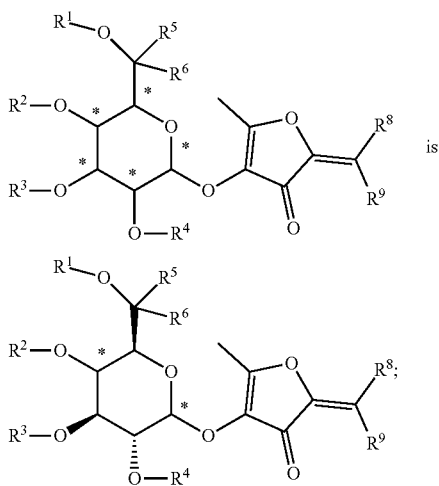

A-1 is or, the structure of the compound represented by formula A is as follows:

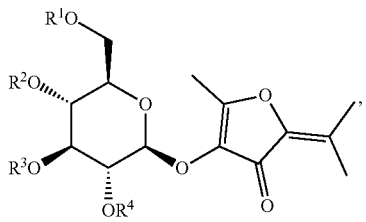

I or a mixture of

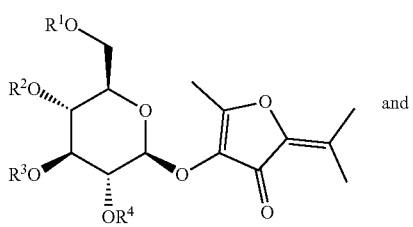

I and

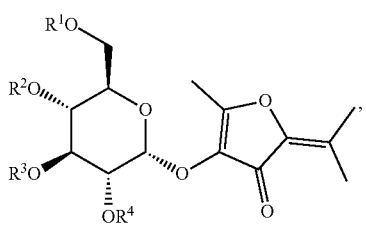

I'

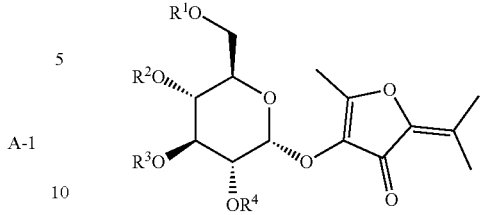

I' in a molar ratio of 1:1.

14. The pharmaceutical composition as claimed in claim 11, wherein $R^1$ is $C_{1\text{-}4}$ alkyl, —C(=O)R, or —C(=O)—O—R';

or, $R^2$, $R^3$, and $R^4$ are independently hydrogen or —C(=O)R;

or, when $R^5$ and $R^6$ are independently hydrogen, then $R^1$ is —C(=O)R or —C(=O)—O—R'; when $R^5$ and $R^6$ are taken together to form =O, then $R^1$ is $C_{1\text{-}4}$ alkyl;

or,

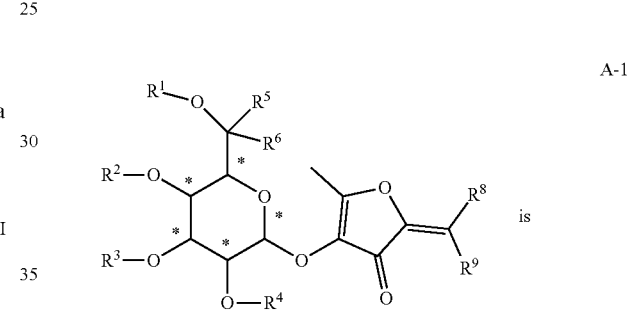

A-1 is or, the structure of the compound represented by formula A is as follows:

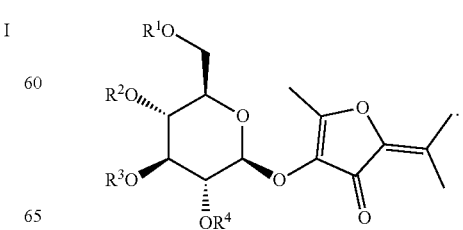

I

15. The pharmaceutical composition as claimed in claim 11, wherein $R^1$ is methyl,
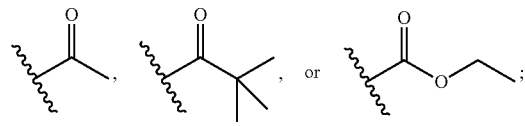
or, $R^2$, $R^3$, and $R^4$ are independently hydrogen
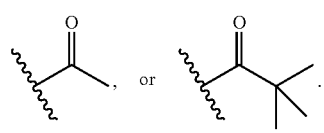
16. The pharmaceutical composition as claimed in claim 11, wherein the structure of the compound represented by formula A-1 is any of the following compounds:
I-1
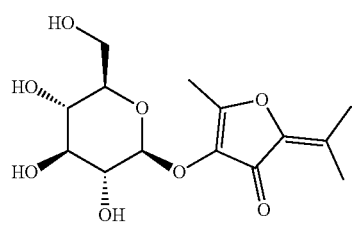
I'-1
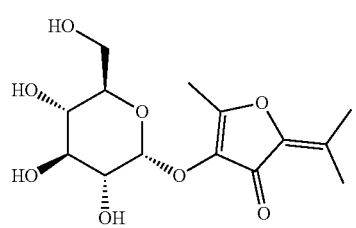
I-2
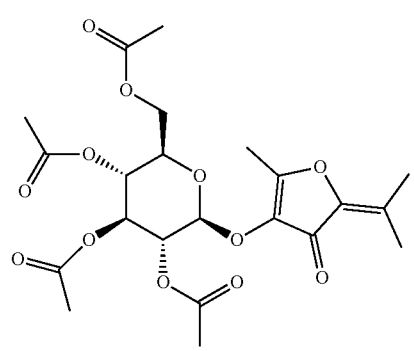
I'-2
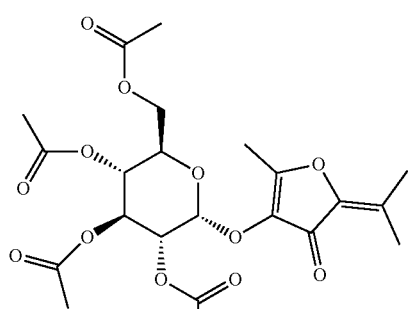
I-4
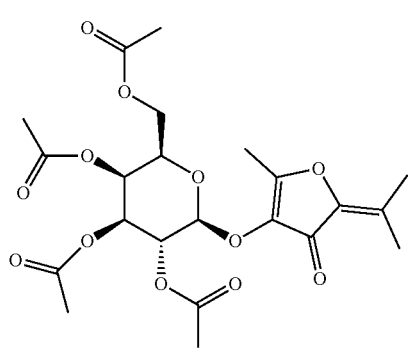
I-5
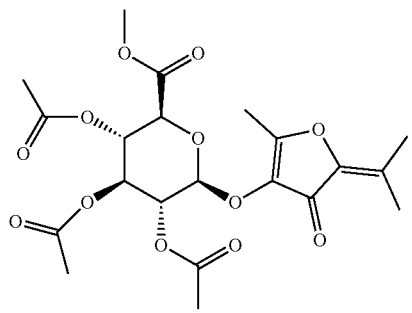
I-6
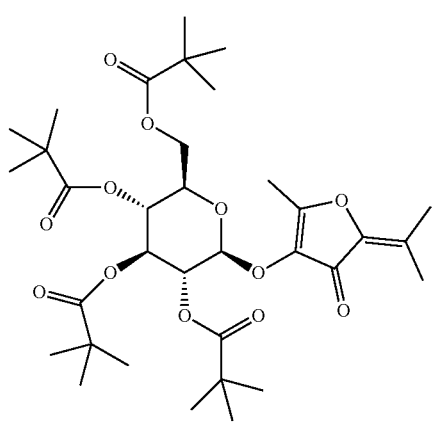

I-7
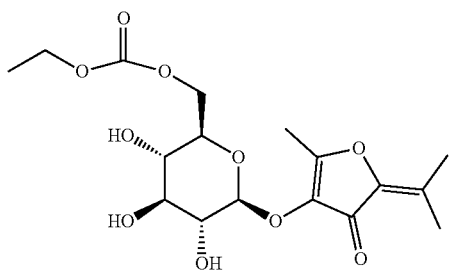
I-8
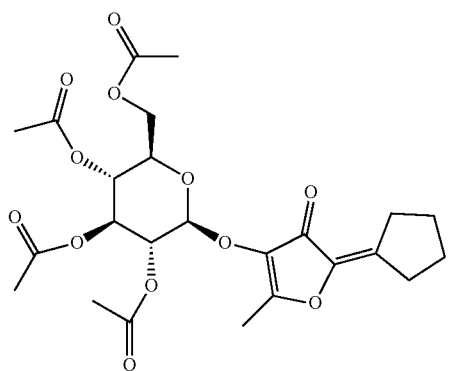
I-9
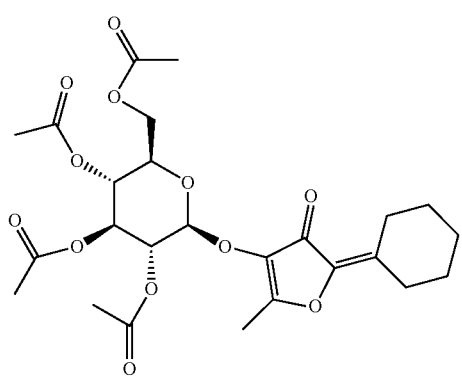
I-10
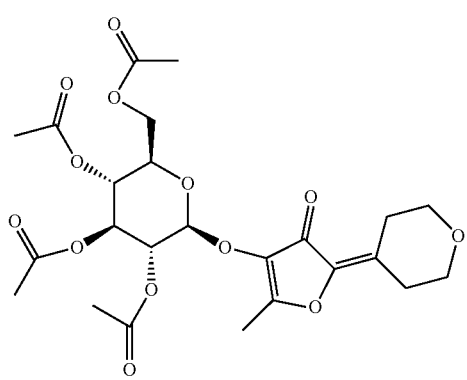
I-11
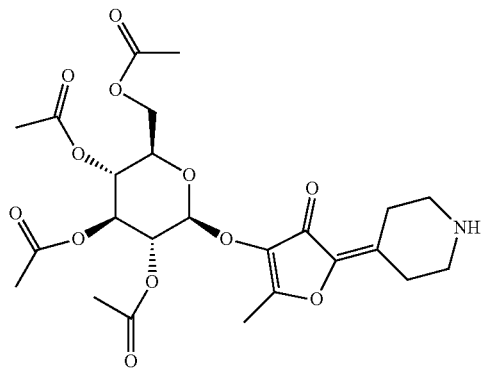
I-12
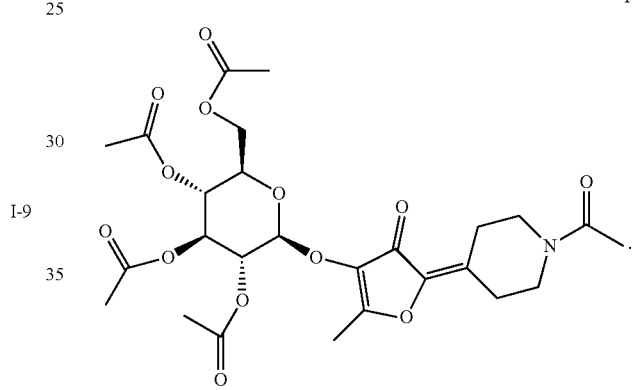
17. A crystal form of a compound represented by formula I-2,
I-2
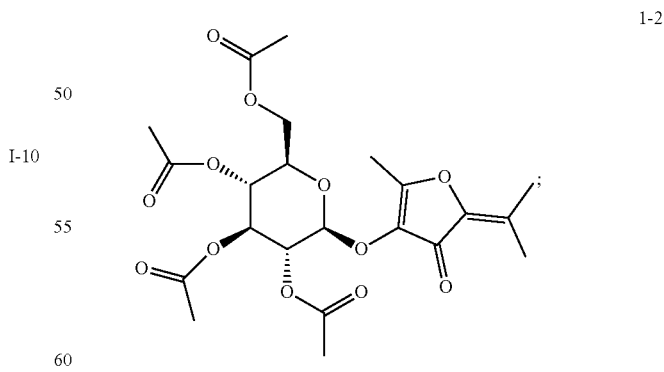
the unit cell parameters of the compound represented by formula I-2 are: a=10.5391(3) Å, α=90°; b=14.2167(4) Å, β=90°; c=15.9116(5) Å, γ=90°; space group $P2_12_12_1$.

18. A pharmaceutical composition comprising the crystal form of the compound represented by formula I-2 as claimed in claim 17 and a pharmaceutical adjuvant.

19. A method of treating inflammatory bowel disease, comprising administrating a therapeutically effective amount of substance A to a patient;

the substance A comprises a compound represented by formula A-1, a pharmaceutically acceptable salt thereof, a solvate thereof, a crystal form thereof, or a pharmaceutical composition thereof;

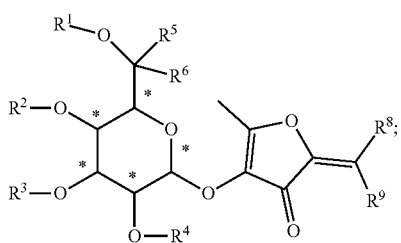

A-1 wherein $R^1$, $R^2$, $R^3$, and $R^4$ are independently hydrogen, $C_{1-4}$ alkyl, benzyl, —C(=O)R, or —C(=O)—O—R';
each R' is independently $C_{1-4}$ alkyl;
each R is independently $C_{1-4}$ alkyl or phenyl;
$R^5$ and $R^6$ are independently hydrogen, or $R^5$ and $R^6$ are taken together to form =O;
$R^8$ and $R^9$ are independently $C_{1-4}$ alkyl;
alternatively, $R^8$ and $R^9$ are taken together with the carbon atom to which they are attached to form 3- to 7-membered cycloalkyl, 3- to 7-membered heterocycloalkyl, 3- to 7-membered cycloalkyl substituted with one or a plurality of $R^a$, or 3 to 7-membered heterocycloalkyl substituted with one or a plurality of $R^b$, in the 3- to 7-membered heterocycloalkyl and the 3- to 7-membered heterocycloalkyl substituted with one or a plurality of $R^b$, the heteroatoms in the 3- to 7-membered heterocycloalkyl are independently selected from N, O, and S, and the number of heteroatoms is independently 1, 2, or 3;
$R^a$ and $R^b$ are independently $C_{1-4}$ alkyl, —C(=O)R'';
each R'' is independently $C_{1-4}$ alkyl;
carbon atoms marked with "*" indicate that when the carbon atoms are chiral, the carbon atoms are in the R-configuration, S-configuration, or a mixture of configuration and S-configuration.

* * * * *